US006120777A

United States Patent [19]

Thiele et al.

[11] Patent Number: 6,120,777
[45] Date of Patent: *Sep. 19, 2000

[54] HIGH FLUORESCENCE SPECIFIC IMMUNE ENHANCING FACTOR AND METHODS OF USE FOR SAME

[75] Inventors: Geoffrey M. Thiele; Thomas L. McDonald; Dean J. Tuma; Lynell W. Klassen; Michael F. Sorrell, all of Omaha, Nebr.

[73] Assignee: The Board of Regents of the University of Nebraska, Lincoln, Nebr.

[ * ] Notice: This patent is subject to a terminal disclaimer.

[21] Appl. No.: 08/849,024

[22] PCT Filed: Oct. 25, 1996

[86] PCT No.: PCT/US96/17240

§ 371 Date: May 27, 1997

§ 102(e) Date: May 27, 1997

[87] PCT Pub. No.: WO97/15324

PCT Pub. Date: May 1, 1997

Related U.S. Application Data

[60] Provisional application No. 60/005,959, Oct. 27, 1995.

[51] Int. Cl.[7] .......................... A61K 39/00; A61K 45/00; C07D 213/00
[52] U.S. Cl. ..................... 424/278.1; 424/184.1; 424/9.1; 530/402; 530/403; 530/405; 530/406; 546/1; 546/314
[58] Field of Search ................................ 514/2; 530/363, 530/402, 403, 405, 406; 546/1, 315; 424/9.1, 184.1, 278.1

[56] References Cited

PUBLICATIONS

Tani et al. "Enhancing Effect of Malondialdehyde Modification on the Mouse IgE Response to Protein Antigens", *Agric. Biol. Chem*, 1990, vol. 54:9 pp. 2323–2330.

Nair et al. "Novel Fluorescent 1,4–Dihydropyridines", *Journ. Am. Chem. Soc.*, 1986, vol. 108:No. 26 pp. 8283–8285.

Kikugawa et al. "Determination of Malondialdehyde in Oxidized Lipids by the Hantzsch Fluorometric Method", *Analytic Biochemistry*, 1988, vol. 174, pp. 512–521.

Beppu et al., "Interaction of Malondialdehyde–Modified Bovine Serum Albumin and Mouse Peritoneal Macrophages", *Chem. Pharm. Bull.*, 1988, vol. 36, No. 11, pp. 4519–4526.

Ohya, Takeshi, "Formation of a New 1,1,1 Adduct in the Reaction of Malondialdehyde, n–Hexylamine and Alkanal under Neutral Condtions", *Biol. Pharm. Bull.*, 1993, vol. 16(2) 137–141.

Bosron, et al., "Genetic Polymorphism of Enzymes of Alcohol Metabolism and Susceptibility to Alcoholic Liver Disease", *Molec. Aspects Med.*, 1988, vol. 10, pp. 147–158.

Groopman, John D., et al., "Molecular Biomarkers for Human Chemical Carcinogen Exposures", *Chem. Res. Toxicol.*, 1993, vol. 6, pp. 764–770.

*Primary Examiner*—Keith D. MacMillan
*Assistant Examiner*—P. Ponnaluri
*Attorney, Agent, or Firm*—Zarley, McKee, Thomte, Voorhees & Sease

[57] ABSTRACT

The present invention relates to a malondialdehyde-acetaldehyde adduct which acts as a specific immune-enhancing factor. In addition to its highly specific and immunogenic properties, the factor is highly fluorescent. It has an excitation frequency of about 398 nanometers and an absorbance of about 460 nanometers. The factor is also highly reactive and is also adducted to antigens including complex proteins, lipids, carbohydrates or DNA.

16 Claims, 9 Drawing Sheets

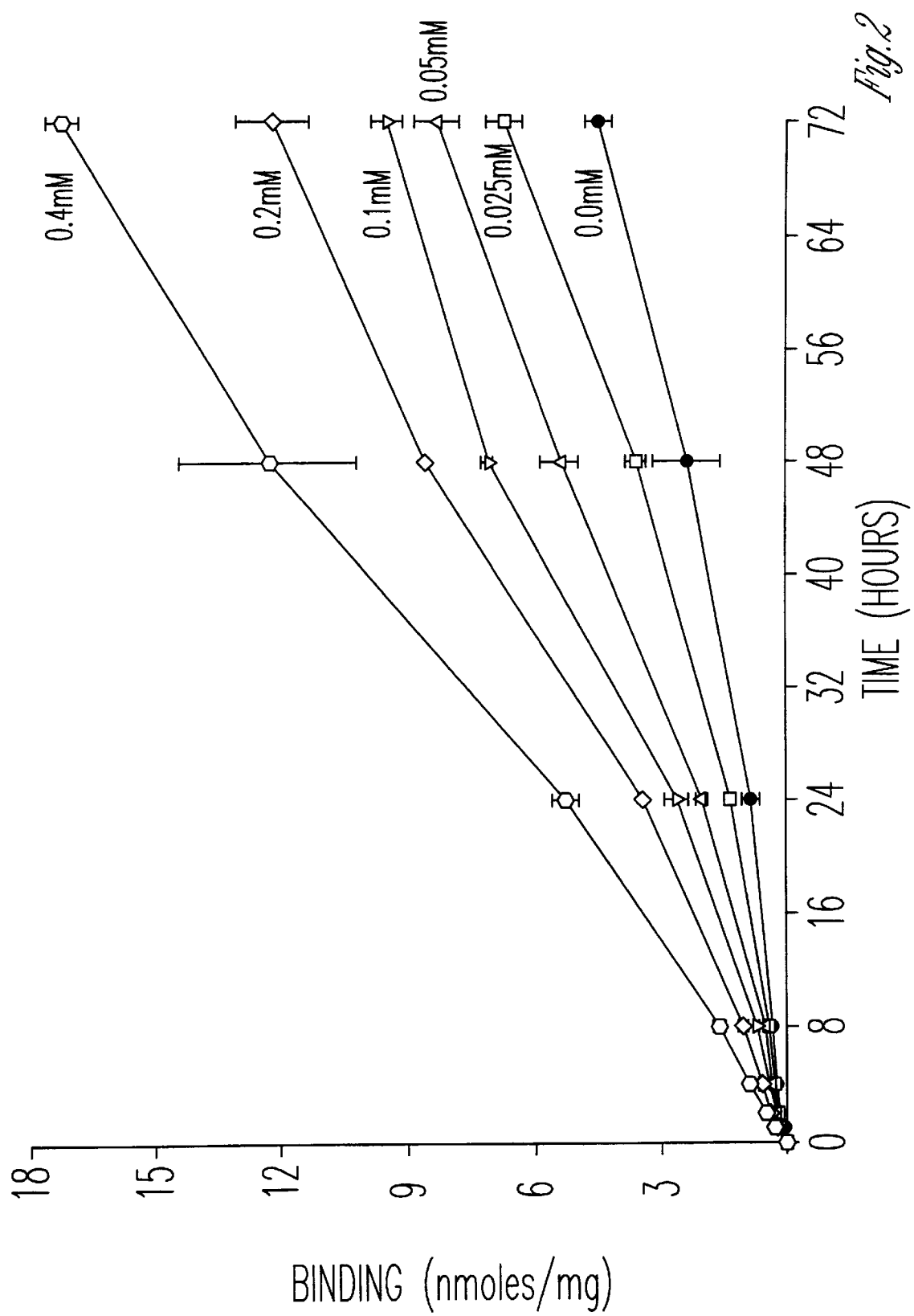

HIGH FLUORESCENCE SPECIFIC IMMUNE ENHANCING FACTOR AND METHODS OF USE FOR SAME

This application claims benefit of Provisional Application 60/005,959 filed Oct. 27, 1995.

GRANT REFERENCE

Work for this invention was funded in part by a grant from United States National Institute of Health Grant Nos. R01-04961-12 and 2R01-AA07818-04. The United States Government may have certain rights in this invention.

FIELD OF THE INVENTION

This invention relates generally to the field of immunology and to a novel specific immune enhancing factor as well as immunochemical and cellular techniques using the unique properties of this factor.

BACKGROUND OF THE INVENTION

This invention relates to a composition for use as a specific immune enhancing factor in therapy for vaccination as well as production of antibodies for harvesting. The composition of the invention is capable of potentiating in vivo the specific antibody response to antigens having low immunogenicity. The composition may be delivered in solution with a pharmacologically acceptable solvent.

Antigens are defined as any substance which is foreign to a living organism and which, on coming into contact with the immune system thereof, activate a complex mechanism of cellular interactions which tend to eliminate the antigen and restore the previous equilibrium. Antigen as the term is used herein shall include proteins, lipids, DNA or carbohydrates. Characteristic features of an antigen are the capacity to induce production of specific antibodies (immunogenicity) which are capable of selectively binding to it (antigenicity) and inactivating it. Some antigens, however, have low immunogenicity and stimulate an antibody response in vivo which is insufficient to give effective immunity to the organism, or to provide sufficient antibodies for harvesting and preparation of polyclonal and monoclonal antibodies. The immune response to an antigen which is administered to a host can be enhanced by the use of adjuvants. An adjuvant is any substance which nonspecifically enhances the immune response to an antigen.

The immune response is mediated by a variety of cells in the immune system. There are two types of immune response: humoral immunity mediated by antibodies, (specific immunity) and cellular immunity mediated primarily by cytotoxic T-lymphocytes. Antigen presenting cells possess and present antigen to both B and T cells. The B cell secretes specific antibodies as a result of activation and T cells (either helper cells to the humoral response or cytotoxic T-cells) respond. Adjuvants have been shown to augment both immune responses. Initial presentation of an antigen induces both IgM and IgG antibodies forming the primary response. This production of antibodies may fall off, however, over time. A secondary response which principally involves the production of IgG antibodies may be triggered by the secondary or later-in-time presentation of the antigen. This generation of a specific immune response generally takes a second inoculation of antigen or even a series of inoculations over several weeks. This is so for even highly immunogenic proteins and additional problems are encountered with less immunogenic compounds. A secondary or even primary response, however, is not guaranteed merely by priming the host with an antigen.

The immunogenicity of an antigen can be improved if it is administered together with adjuvants such as killed bacteria or immunologically inert substances which are capable of increasing the concentration of the antigens presented to the immune system. Adjuvants enhance the immune system response when administered with an antigen, producing higher antibody titers and prolonged host response. The most commonly used adjuvant is Freund's adjuvant. Incomplete Freund's adjuvant comprises a water and oil emulsion and Freund's complete adjuvant which comprises the above with the addition of Microbacterium tuberculosis and alum. Freund's adjuvant, however, has several disadvantages in that it often causes acute pain and may cause the host to develop lesions at the site of injection.

Another commercially available adjuvant with wide use is monophosphoryl lipid A (MLP)/trehalose dicorynomycolate (TDM) (Ribi Immunochem. Research, Inc., Hamilton, Mont.). Alum and aluminum hydroxide have also been used as an alternative to Freund's adjuvant, however, these also present problems in view of inefficiency toward synthetic antigens and thymus independent antigens. Further, numerous adjuvants of bacterial or chemical origin have been proposed in the prior art but few are both highly efficient and free from side effects and none have been found to enhance only specific immunity.

It is therefore an object of the present invention to provide a factor which specifically enhances the immune response to a particular antigen creating a high antibody titer, and reducing time course for production of antibody.

Yet another object of the present invention is to provide a hapten which can be adducted to any carrier and cause it to become immunogenic.

It is yet another object of the present invention to provide a factor with high fluorescence which can be used for labeling and detecting presence of antibodies or other complex biomolecules in any of a number of available immunochemical techniques.

Other objects of the invention will become dear from the detailed description of the invention which follows.

SUMMARY OF THE INVENTION

This invention discloses a novel reactant product of acetaldehyde (AA) and malondialdehyde (MDA) which interact together forming a novel compound which is highly reactive and is also adducted to antigens including complex proteins, lipids, carbohydrates or DNA simply by incubation of the two aldehydes with the antigen. The combination of MDA and acetaldehyde in the presence of various antigens causes a formation of a new distinct product comprising a hybrid adduct of MDA and acetaldehyde which has been designated malondialdehyde, acetaldehyde-adduct (MAA). These hybrid adducts are novel and the general chemical formula has been characterized. This is in stark contrast to most adducts which have not been so delineated, and provides opportunities for independent synthesis of the adduct itself and for creation of new antigen adduct combinations, as well as alternative assay methods.

According to the invention, the combination of MDA and AA in the presence of a protein or peptide creates two hybrid adducts which have been characterized at the molecular level having the following formulas. The hybrid adducts of the invention can include alterations at various functional groups which would not be expected to change the overall reactivity of the product. The formula for these hybrid adducts is listed below.

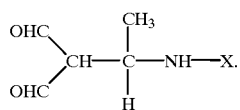

Wherein X is an antigen selected from the group consisting of a protein or peptide, a lipid, a carbohydrate which contains a reactive amino residue.

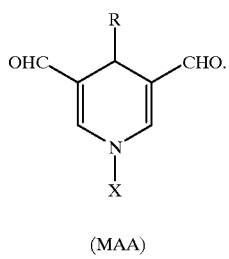

Wherein R is a $C_1$ to about $C_6$ alkyl, H, Benzyl or aryl group and X is an antigen selected from the group consisting of a protein or peptide, a lipid, a carbohydrate which contains a reactive amino residue. These hybrid adducts are formed under standard conditions, by simple incubation.

In addition to the above-identified novel hybrid adducts, the adducts of the invention have several important immunological properties which can be exploited for further chemical and immunological assay procedures.

MAA is highly reactive and will bind antigens preferentially to either acetaldehyde or malondialdehyde alone. It will form adducts at standard conditions by mere combination of the aldehydes and a carrier antigen. Adducts have been formed with bovine serum albumin, human serum albumin, ovalbumin, Hen egg lysozyme, asialoglycoprotein receptor, actin, rat liver microsomes, rat liver cytosol, human epidermal growth factor, mouse epidermal growth factor, transferrin, antibodies and hemoglobin as well as numerous other hepatic proteins and there appears to be no limit to proteins which will form an adduct. These adducts can then be used as an immunogen, either for a vaccine for animal or human based antigens or for harvesting of antibodies. For example, MAA could be used with environmentally derived antigens to desensitize allergy patients. MAA acts as a specific immunoenhancing factor allowing for shorter time course for production of antibody, and higher titer antibodies without the need for adjuvant, also decreasing the amount of antigen needed for response. An IgG response can be observed in as little as three days with a single inoculation.

In addition to the highly specific and immunogenic properties, MAA is highly fluorescent. It has an excitation frequency of 398 nanometers and an absorbance of 460 nanometers, and can be detected at picomolar levels. Tests have shown that MAA adduction does not deactivate antibodies when adducted and it can be used for a general fluorescent label for all kinds of immunological techniques including identification and visualization of antigen-antibody interactions by labeling either with MAA. It can also be used as a universal label for visualization of protein interactions and for monitoring purification of biological reactions.

DESCRIPTION OF THE FIGURES

FIG. 2 is a graph depicting the stability of the interaction between acetaldehyde and MDA. The graph depicts acetaldehyde at 0.1 mM incubated with BSA 1 mg/ml at 37° C. in the absence and presence of MDA (0.2 to 0.4 mM) over 72 hours and there was still a synergistic effect. Results and mean +SE for four experiments.

FIG. 3(a) depicts the relative fluorescence over an 8 hour time course with acetaldehyde (1.0 mM) and BSA (1 mg/ml) at 37° C. at various concentrations of MDA (0 to 8.0 mM). Results are mean +SE for five experiments.

FIG. 4(a) demonstrates specificity of the antibody. BSA was reacted for 3 days with acetaldehyde alone (1 mM)(circle); MDA alone (1 mM)(square); acetaldehyde (1 mM) and MDA (1 mM)(triangle) and native (untreated) BSA (inverted triangle).

FIG. 4(b) represent direct ELISA of the polyclonal antibody the affinity in the presence of 0.1 mM concentration of the aldehydes separately and together. As can be seen, the results are that of a typical ELISA demonstrating specificity of the affinity purified antibody to MAA adducts.

(square); 0.70 (diamond); 0.54 (triangle); and 0.48 (inverted triangle). 7(a) is percent inhibition in terms of protein concentration and 7(b) percent inhibition as a function of bound acetaldehyde.

Figure 8A:
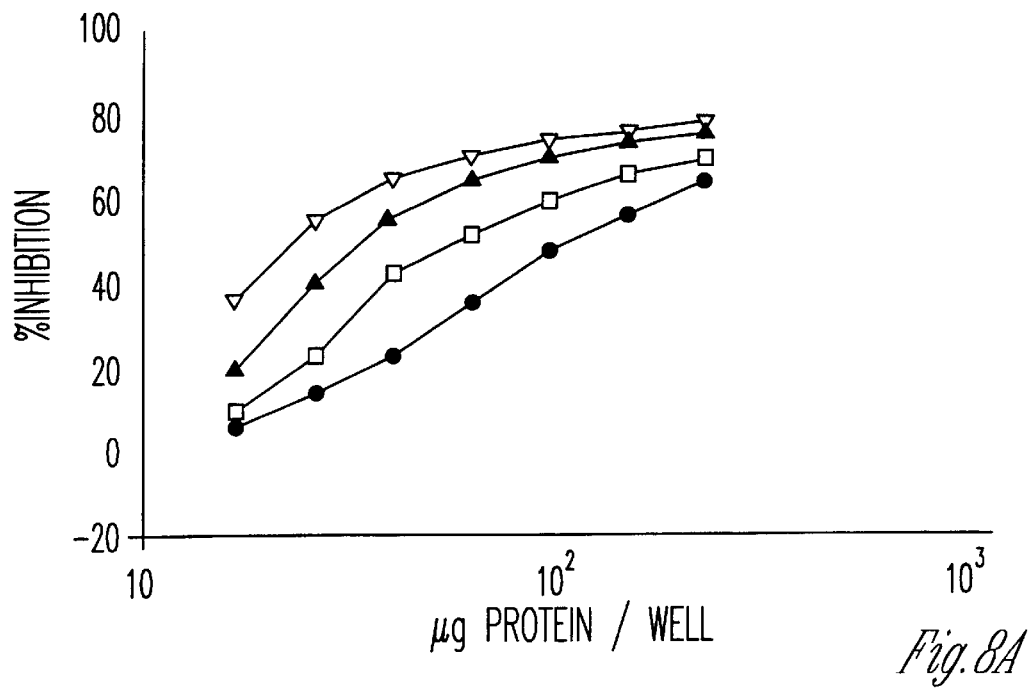

FIG. 8(a) is a graph depicting a competitive ELISA of minimally modified liver cytosolic protein-MAA adducts. Conditions were as in FIG. 6. Percent inhibition based on nmoles of acetaldehyde bound per mg of protein: 5.0 (inverted triangle); 2.5 (triangle); 1.1 (square); and 0.49 (circle). In 8(a) the percent inhibition is a plot as a function of protein concentration.

Figure 8B:
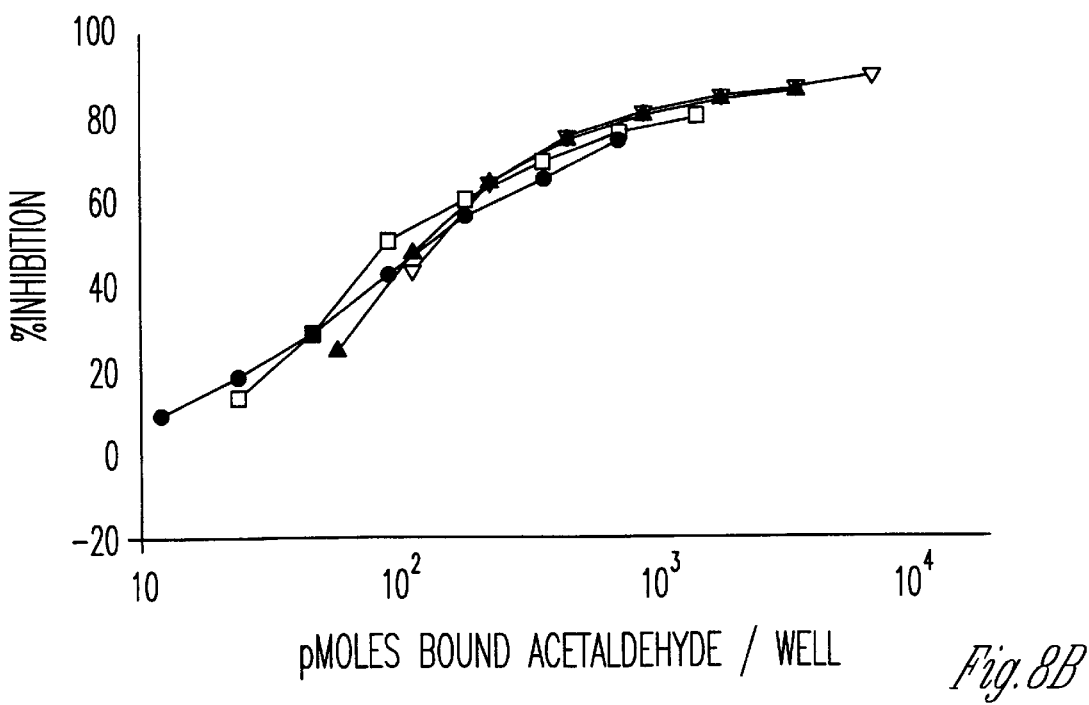

FIG. 8(b) is the data plotted as a function of bound acetaldehyde.

Figure 9A:
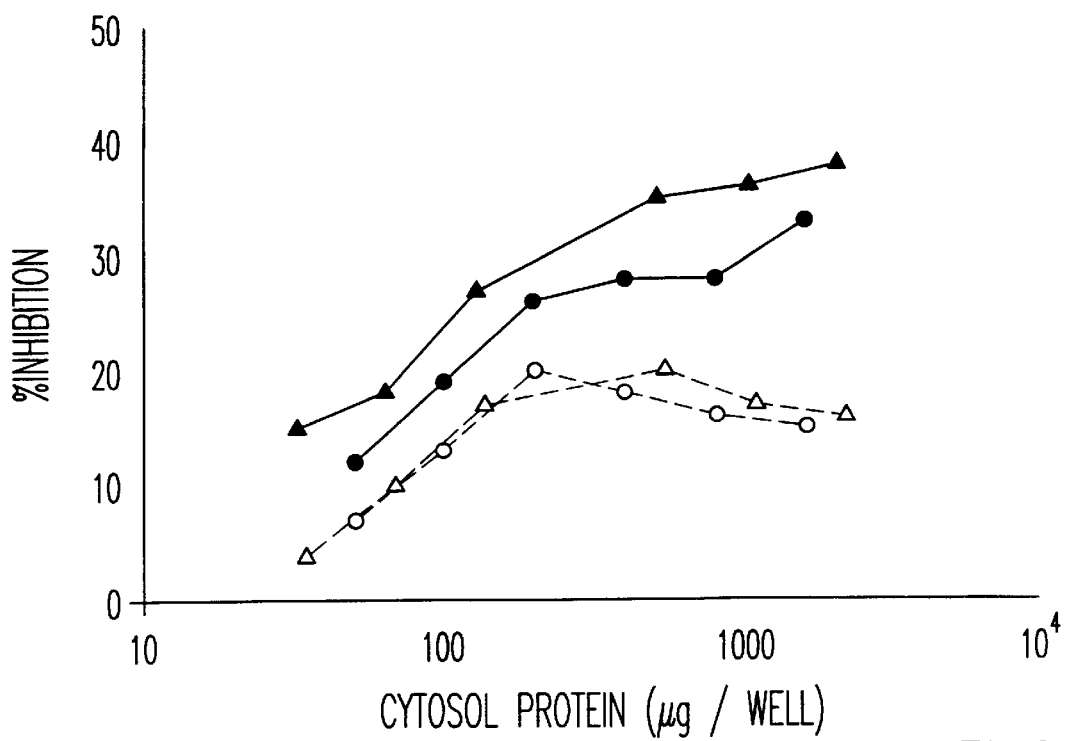

FIG. 9(a) depicts a competitive ELISA for detection of MAA adducts in liver cytosol from two ethanol-fed rats. Percent inhibition representing cytosol from ethanol fed rats (shaded triangle and circle) and their corresponding pair fed control (open circle and triangle).

Figure 9B:
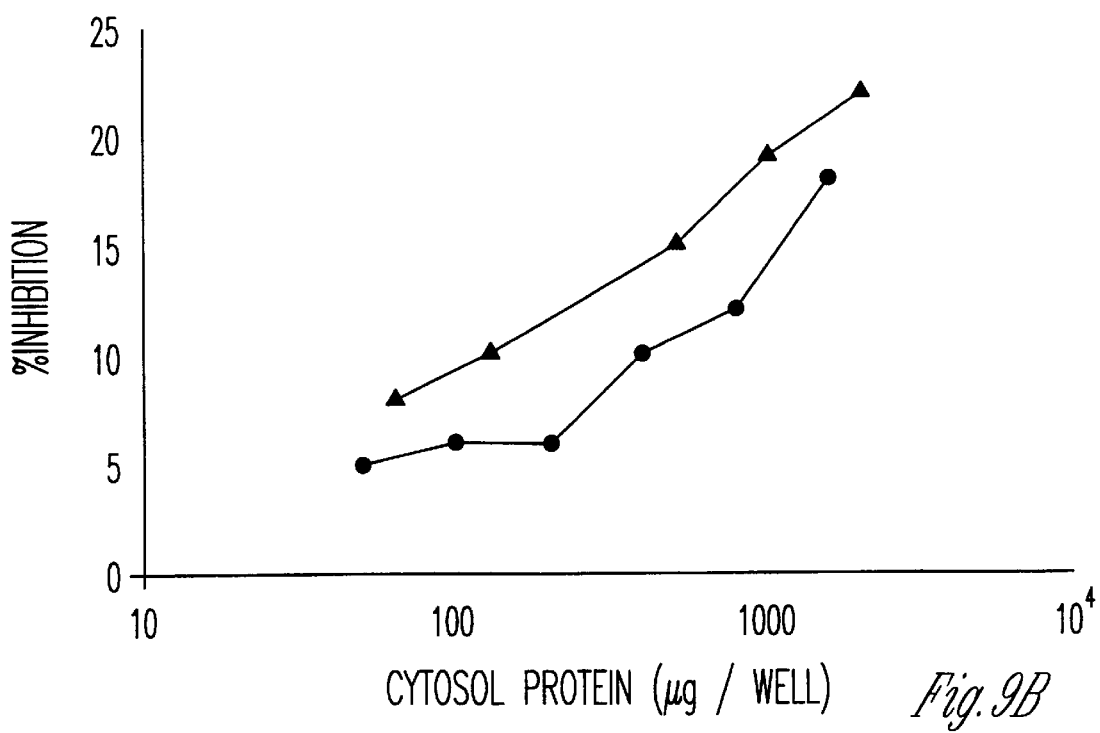

FIG. 9(b) represents the data from 9(a) with the control inhibition value subtracted.

DETAILED DESCRIPTION OF THE INVENTION

Studies involving the chemistry of acetaldehyde protein adduct formation have shown that acetaldehyde forms both unstable and stable adducts and that the ε-amino group of lysine participates in binding for formation of the adducts. It has also been found that proteins contain lysine residues with varying reactivities towards acetaldehyde adduct formation and that certain proteins are selective targets for adduct formation in cellular systems by virtue of containing a specially reactive key lysine residue.

On the other hand malondialdehyde (MDA) is formed by the peroxidation of polyunsaturated fatty acids and from the oxidative degradation of deoxyribose by a hydroxy radical. The nature and/or chemical structures of these adducts that form in vitro and in vivo have not been characterized and conflicting results in the literature concerning the nature of subcellular distribution and identity of the adducts have been reported. See Tuma, DJ, "The Roll of Acetaldehyde Adducts in Liver Injury", Hall P. editors, Alcoholic Liver Disease: Pathology and Pathogenesis, ed. II, London: Edward Arnold, 1995, 89–99. This invention relates to the discovery of novel adducts which are a hybrid of malondialdehyde and acetaldehyde. According to the invention these two products combine to form highly immunogenic antigen adducts, one of which is denoted as malondialdehyde-acetaldehyde-adduct or (MAA), a second is a less stable adduct (I.).

The novel hybrid adducts of the invention are formed at neutral standard conditions, both in vitro and in vivo. The adducts are formed according to the following formulas wherein X is a soluble protein present in a biological sample and R is a lower alkyl, benzyl, or hydrogen.

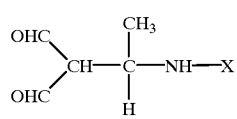

I

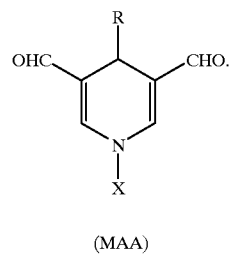

(MAA)

Applicants have demonstrated that the presence of AA and MDA with proteins results in a dramatic increase in protein adduction, even at concentrations as low as 0.1 mM acetaldehyde and 0.2 mM malondialdehyde. Malondialdehyde and acetaldehyde together increased protein adduction 13 times that of acetaldehyde alone. Amino groups of antigens especially the ε-amino group of internal lysines are the major functional group participating in MAA adduction, and adduction occurs with numerous amino group sources such as lipids, DNA, RNA, carbohydrates, etc.

Acetaldehyde and malondialdehyde can combine to form a product that is modified almost ten-fold higher than MDA alone in the presence of an antigen substrate and form under neutral conditions. Thus, MDA and AA react together in a synergistic manner under neutral conditions generating a higher amount of antigen adducts. These novel adducts possess a number of unique immunological and chemical properties which can be exploited according to the invention.

In one embodiment, the invention comprises use of MAA-adducted antigens as an immunogen. MAA will form a stable adduct with virtually any antigen including bovine serum albumin, human transferrin, human hemoglobin, other hepatic proteins and plasma proteins. It can ben used to inoculate animals with environmental, animal or human based antigens, to provide disease resistance or to inhibit allergic reactions.

These MAA adducts are highly immunogenic, and act as a specific immunoenhancer. Antibody responses to MAA-protein adducts in autologous systems result in high antibody titers to only MAA, but not to the protein. Thus, unlike many hapten conjugates, MAA does not create autoimmune disease. Normal plasma proteins in autologous animals generates no antibody response. In a heterologous system MAA adducted proteins injected into animals yields high-titer antibody with no adjuvant to both the protein and MAA, in the absence of adjuvant.

T-helper cell response in autologous systems resulted in no T-helper cells to MAA, however, a T-helper cell response to normal plasma proteins is detected. In heterologous systems proteins injected into mice which generate no T-helper cell response; however when adducted to MAA generate a T-helper cell response to the carrier but not to MAA (hapten).

MAA induces high titers of antibodies without adjuvant and ab can be detected with injection of as little as 10 μg of conjugate. It specifically targets the conjugated protein to become immunogenic and does not generate a nonspecific polyclonal-activation type of a response, but a specific antibody response, with virtually no cross reactivity with even closely related antigens. An IgG response can be seen in as few as three days.

One method involves exploitation of the immunogenicity of the MAA-conjugate by developing monoclonal and polyclonal antibodies to all kinds of carrier proteins for use in immunological quantifications. In principle, all current immunoassays such as radioimmunoassay, enzyme immunoassay, fluorescence immunoassay, etc. are suitable for the immunological method and determination according to the present invention. In addition all variants of the procedure such as competitive immunoassay are applicable.

Because MAA is a specific immune enhancing factor, traditional methods of polyclonal antibody generation consisting of closely related antibodies with high cross reactivity are lessened.

Polyclonal antibodies to the MAA adduct generally are raised in animals by multiple subcutaneous (sc) or intraperitoneal (ip) injections of the MAA protein adduct and an adjuvant. As is demonstrated herein, the MAA adduct is highly immunogenic and can act as a specific immune enhancing factor causing carrier proteins to become immunogenic. In fact the MAA-adduct, as a specific immune enhancing factor, works better than nonspecific adjuvants in generating high titer antibodies, so efficient that the IgG titer may be observed after fewer injections. Many antigens require purification of the protein or peptide and conjugation thereof to a second protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Quite unexpectedly, these types of protocols are not necessary for the MAA-adducts as MAA itself is highly immunogenic.

Animals ordinarily are immunized against the cells or immunogenic conjugates of MAA with monophosphoryl lipid A (MLP)/trehalose dicorynomycolate (TDM) (Ribi Immunochem. Research, Inc., Hamilton, Mont.) and injecting the solution intradermally at multiple sites. Two weeks later the animals are boosted with the original amount of conjugate in MPL/TDM. 7 to 14 days later animals are bled and the serum is assayed for anti MAA titer. Animals are boosted until the titer plateaus. Aggregating agents such as alum are often used to enhance the immune response. Again, the MAA adduct is so immunogenic it can generate a IgG response in as little as 3 days, and adjuvants such as MPL/trehalose dicorynomycolate (TDM), or Freunds may not be necessary.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, *Eur. J. Immunol.*, 6:511 (1976) and also described by Hammerling et al., in "Monoclonal Antibodies and T-Cell Hybridomas, Elsevier, N.Y., pp. 563–681 (1981) has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a medium containing hypoxanthine-aminopterin thymidine (HAT). In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion-exchange chromatography, affinity chromatography such as protein A/protein G column chromatography, or the like. The antibodies described herein are also recovered from hybridoma cell cultures by conventional methods such as precipitation with 50% ammonium sulfate. The purified antibodies can then be sterile filtered.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. All monoclonal and polyclonal antibodies including hybridomas are maintained at the VA Medical Center in Omaha, Nebr.

The monoclonal antibodies herein also include hybrid and recombinant antibodies produced by splicing a variable (including hypervariable) domain of an anti-MAA antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g. Cabilly, et al., U.S. Pat. No. 4,816,567; Mage & Lamoyi, in "Monoclonal Antibody Production Technique and Applications", pp. 79–97 (Marcel Dekker, Inc., New York, 1987).)

Thus, the modifier "monoclonal" indicates the character of the antibody as being obtained from a substantially homogenous population of antibodies, and is not to be construed as requiring production of the antibody by any particular method. For example, the monoclonal antibodies to be used in accordance with the present invention may be made by the hybridoma method described by Kohler a Milstein, supra, or may be made by recombinant DNA methods (Cabilly, et al., supra).

Diagnostic Uses of MAA and Anti-MAA Antibodies

Anti-MAA antibodies are useful in diagnostic assays for MAA expression in specific cells or tissues wherein the antibodies are labeled as described below and/or are immobilized on an insoluble matrix. Anti-MAA antibodies also are useful for the affinity purification of the MAA from recombinant cell culture or natural sources. The Anti-MAA antibodies that do not detectably cross-react with other protein or materials, can be used to purify each MAA conjugated protein adduct free from other homologous receptors.

Suitable diagnostic assays for the MAA are well known per se. For example, a biological sample may be assayed for MAA by obtaining the sample from a desired source, admixing the sample with anti-MAA antibody to allow the antibody to form antibody/MAA complex with any MAA present in the mixture and detecting any antibody/MAA complex present in the mixture. The biological sample may be prepared for assay by methods known in the art which are suitable for the particular sample. The methods of admixing the sample with antibodies and the methods of detecting antibody/MAA complex are chosen according to the type of assay used. Such assays include competitive and sandwich assays, and steric inhibition assays. Competitive and sandwich methods employ a phase-separation step as an integral part of the method while steric inhibition assays are conducted in a single reaction mixture.

Analytical methods for the MAA all use one or more of the following reagents: labeled MAA analogue, immobilized MAA analogue, labeled anti-MAA antibody, immobilized anti-MAA antibody and steric conjugates. Because MAA has high fluorescence and does not affect activity of antibodies, MAA itself can be used as a label for its own detection, or for detection of other antibodies by conjugating the antibody, or protein to it and using fluorescence detection. The labeled reagents also are known as "tracers."

The label used is any detectable functionality that does not interfere with the binding of MAA and anti-MAA antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbondiamides, dimaleimides, bisimidates, bis-diazotized benzidine, and the like may be used to tag the antibodies with the above-described fluorescent, chemiluminescent, and enzyme labels. See, for example, U.S. Pat. No. 3,940,475 (fluorometry) and U.S. Pat. No. 3,645,090 (enzymes); Hunter et al., *Nature*, 144:945(1962); David et al., *Biochemistry*, 13:1014–1021 (1974); Pain et al., *J. Immunol. Methods*, 40:219–230 (1981); and Nygren, *J. Histochem. and Cytochem.*, 30:407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-Antibody Conjugates for Use in Enzyme Immunoassay", in *Methods in Enzymology*, et. J. J. Langone and H. Van Vunakis, Vol. 73 (Academic Press, New York, N.Y., 1981), pp. 147–166.

Thus, the invention in an alternative embodiment contemplates a novel label which can be used with immunoassay protocols. Conjugation of the MAA label to the antibody is greatly simplified. As earlier described, the antibody is merely co-incubated with acetaldehyde and malondialdehyde.

Immobilization of reagents is required for certain assay methods. Immobilization entails separating the anti-MAA antibody (from MAA adducted protein immunogen) from any MAA that remains free in solution. This conventionally is accomplished by either insolubilizing the anti-MAA antibody or MAA analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-MAA antibody or MAA analogue afterward, e.g., by immunoprecipitation.

Other assay methods, known as competitive or sandwich assays, are well established and widely used in the commercial diagnostics industry.

Competitive assays rely on the ability of a tracer MAA analogue to compete with the test sample MAA for a limited number of anti-MAA antibody antigen-binding sites. The anti-MAA antibody generally is insolubilized before or after the competition and then the tracer and MAA bound to the anti-MAA antibody are separated from the unbound tracer and MAA. This separation is accomplished by decanting (where the binding partner was preinsolubilized) or by centrifuging (where the binding partner was precipitated after the competitive reaction). The amount of test sample MAA is inversely proportional to the amount of bound tracer as measured by the amount of marker substance. Dose-response curves with known amounts of MAA are prepared and compared with the test results to quantitatively determine the amount of MAA present in the test sample. These assays are called ELISA systems when enzymes are used as the detectable markers.

Another species of competitive assay, called a "homogeneous" assay, does not require a phase separation. Here, a conjugate of an enzyme with the MAA is prepared and used such that when anti-MAA antibody binds to the MAA the presence of the anti-MAA antibody modifies the enzyme activity. In this case, the MAA or its immunologically active fragments are conjugated with a bifunctional organic bridge to an enzyme such as peroxidase. Conjugates are selected for use with anti-MAA antibody so that binding of the anti-MAA antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small MAA fragment so that antibody to hapten is substantially unable to bind the conjugate at the same time as anti-MAA antibody. Under this assay procedure the MAA present in the test sample will bind anti-MAA antibody, thereby allowing anti-hapten to bind the conjugate, resulting in a change in the character of the conjugate hapten, e.g., a change in fluorescence when the hapten is a fluorophore.

Sandwich assays particularly are useful for the determination of MAA or anti-MAA antibodies. In sequential sandwich assays an immobilized anti-MAA antibody is used to adsorb test sample MAA, the test sample is removed as by washing, the bound MAA is used to adsorb a second, labeled anti-MAA antibody and bound material is then separated from residual tracer. The amount of bound tracer is directly proportional to test sample MAA. In "simultaneous" sandwich assays the test sample is not separated before adding the labeled anti-MAA A sequential sandwich assay using an anti-MAA monoclonal antibody as one antibody and a polyclonal anti-MAA antibody as the other is useful in testing samples for MAA.

The foregoing are merely exemplary diagnostic assays for MAA. Other methods now or hereafter developed that use anti-MAA antibody for the determination of MAA are included within the scope hereof, including the bioassays described above.

The MAA adduct itself is highly fluorescent with an excitation frequency of 398 nanometers and an absorbance of 460. It is one of the most fluorescent products ever encountered and allows for detection of fluorescence at a picomolar range for detection of presence of antibody antigen complexes or antigen itself.

Another embodiment of the invention comprises use of a hybrid protein adduct which can be used in labeled antibody procedures to visualize antigen antibody interactions by labeling antigens or antibodies. MAA can be used as a label for immunoassays as earlier described but can also be used for visualization of protein-protein interactions and monitoring purification of biological reactions on gels, such as Western blotting or ELISA, on FACScan and other such techniques.

Further, the present invention contemplates that the MAA adduct structures can be modified in various manners in order to make them even more fluorescent. For instance, once the MAA adduct is synthesized, a benzyl group can be substituted for a methyl group in order to enhance its detectability and immunogenicity.

Due to their detectability in the pmolar range, MAA adducts can be used to increase the detection of proteins and could potentially replace $^{125}$I labeling in autoradiography. Further, in conjunction with DNA probes, MAA adducts can be used to replace radioactivity hybridization of the probes.

MAA adducts can further be utilized for the isolation and/or purification of proteins. The MAA adducts could first be used to tag a mixture of proteins and then the separation of the proteins (using standard techniques), could be monitored using the unique flourescent properties of this invention. The adducts would also provide a means of increasing the immunogenicity of the proteins.

All references cited in this specification are hereby expressly incorporated by reference. The following examples are offered by way of illustration and not by way of limitation.

EXAMPLE 1

PREPARATION OF MAA POLYCLONAL ANTIBODY

Materials:

[1,2$^{14}$C] Acetaldehyde (5 mCi/mmole) was purchased from New England Nuclear (Boston, Mass.). Radiolabeled acetaldehyde was received from the manufacturer frozen as an aqueous solution (1 mCi/ml), thawed and diluted to 250 $\mu$Ci/ml with distilled water, rapidly refrozen, and stored at −70° C. The specific activity of the acetaldehyde was checked as described by Miwa et al., "The Direct Oxidation of Ethanol by a Catalase- and Alcohol Dehydrogenase-Free Reconstituted System Containing Cytochrome P-450", Arch Biochem Biophys, 1978; 30:464–475. Bovine serum albumin (BSA) (crystallized, lyophilized, and fatty acid free) was obtained from Sigma Chemical Co. (St. Louis, Mo.). Nonradioactive acetaldehyde was purchased from Aldrich Chemical Co. (Milwaukee, Wis.). MDA was obtained as the sodium salt (MDA•Na) by treatment of tetramethoxypropane (Aldrich) with NaOH according to the method of Kikugawa and Ido. "Studies on Peroxidized Lipids. V. Formation and Characterization of 1,4-Dihydrophyridine-3, 5-Dicarbaldehydes as Model of Fluorescent Components in Lipofusion", Lipids, 1984; 19:600–608. All other chemicals were of analytical grade.

Determination of Stable Binding of Acetaldehyde to Proteins in the Presence of MDA:

Concentrations of [$^{14}$C]acetaldehyde (0.1 mM or 1.0 mM) were incubated with various protein solutions in the absence and presence of varying concentrations of MDA. Incubations were conducted in phosphate buffer (0.1 M, pH 7.4) at 37° C. in polypropylene vessels that were sealed to minimize the loss of volatile radioactivity. The reactions were performed under nitrogen gas in the dark. During a 72-hr incubation period, aliquots were removed for stable acetaldehyde binding determinations and fluorescence measurements as previously described. Hoffmann, "Reaction of Acetaldehyde with Proteins: Formation of Stable Fluorescent Adducts", Alcohol Clin Exp Res, 1993; 17:69–74. Briefly, postincubation, free and unstable-bound acetaldehyde were separated by exhaustive dialysis against phosphate buffer for 24 hours at 4° C. Radioactivity was then measured in the retenate and represented stably bound acetaldehyde. Results are expressed as nmoles acetaldehyde bound per mg of protein. Fluorescence measurements were obtained on post-dialysis samples using a Perkin Elmer LS-5B spectrophotofluorometer attached to a Perkin Elmer GP-100 graphics printer.

Preparation, Purification and Biotinylation of Rabbit Polyclonal Antibody to MDA/Acetaldehyde-Modified Proteins:

The immunogen was prepared by the treatment of rabbit plasma proteins (prepared by ammonium sulfate precipitation) Klassen, "Detection of Reduced Acetaldehyde Protein Adducts Using a Unique Monoclonal Antibody", Alcohol Clin Exp Res, 1994; 18:164–171) at a concentration of 1 mg/ml with 1 mM acetaldehyde plus 1 mM MDA for 3 days at 37° C. Following overnight dialysis against 0.1 M phosphate buffer (pH 7.4 and 4° C.), the solution was mixed with an equal volume of Freund's complete adjuvant and emulsified. New Zealand white rabbits were injected subcutaneously in four sites along their backs (400 $\mu$g of modified protein). After two and four weeks, the rabbits were boosted by the same procedure except Freund's incomplete adjuvant was used. Two weeks after the final injection, serum was obtained and tested for antibody activity.

The resulting antisera was then affinity purified. Lysine derivatized Sepharose 4B beads (Sigma Chemical Co., St. Louis, Mo.) were modified by adding acetaldehyde (1 mM) and MDA (1 mM) in 0.1 phosphate buffer, pH 7.4, and incubating at 37° C. for 3 days with constant shaking. The beads were washed with four volumes of buffer and poured into a 0.7 cm×15 cm low pressure Econo-Column (Bio-Rad Laboratories, Hercules, Calif.). Ten ml of rabbit serum from the immunized animals were loaded onto the column. The column was washed with 5 volumes of buffer, followed by 1 M NaC 1, and then eluted with 0.5 M acetic acid (pH 2.5) into Tris buffer (pH 8.2) to neutralize the acid. The eluted material was further purified by Protein G-Sepharose B (Pharmacia, Piscataway, N.J.) column chromatography, yielding a purified IgG fraction of greater than 95%.

The affinity purified antibody was biotinylated by the method of Bayer and Wilchek. Bayer, "The Use of the Avidin-Biotin Complex as a Tool in Molecular Biology", Methods Biochem Anal, 1980; 26:1–46. Briefly, the antibody at 1 mg/ml was dialyzed against 0.1 M sodium borate buffer (pH 8.8) for 4 hours at room temperature. N-hydroxysuccinimide biotin (100 μg) (Sigma Chemical Co., St. Louis, Mo.) was added to this solution and incubated at room temperature for four hours. After this time, the solution was treated with 15 μl of 1 M ammonium chloride for 10 minutes at room temperature, and dialyzed overnight at 4° C. against phosphate buffered saline (PBS)(pH 7.4). The biotinylated antibody was stored at 4° C. until use.

EXAMPLE 2

DIRECT AND COMPETITIVE ENZYME-LINKED IMMUNOSORBENT ASSAYS (ELISA)

A direct ELISA was used to screen the polyclonal rabbit antiserum and ascertain the specificity of the affinity purified antibody. Test proteins were diluted to 20 μg/ml in bicarbonate buffer (pH 9.6), and 100 μl of sample were added to a 96-well ELISA plate (Immulon IV, Nunc, Fisher Scientific, St. Louis, Mo.). After incubation at 37° C. for 1 hour followed by an overnight incubation at 4° C., the coated wells were washed with PBS containing 0.05% Tween-20 (PBST) to remove unbound protein. The biotinylated antibody was then added to the antigen-coated wells and incubated at 37° C. for 1 hour. After washing 3 times with PBST, 100 μl of alkaline phosphatase-conjugated streptavidin (Zymed Laboratories, San Francisco, Calif.) were added, and incubated at room temperature for 10 minutes. The plates were then washed three times with PBST, and 100 μl of the substrate, p-nitrophenyl phosphate (Sigma), were added. Optical density at 405 nm was measured by a Dynatech Micro ELISA Reader MR7000 (Dynatech, Chantilly, Va.).

A competitive ELISA was developed in order to detect the presence and to quantify the level of MDA/acetaldehyde modified proteins. Following the basic methodology developed by Roberts, et al, "A Sensitive Immunochemical Assay for Acetaminophen-Protein Adducts", *J Pharmacol Exp Ther*, 1987; 241:527–533; Pumford, et al, "Immunochemical Quantitation of 3-(cystein-S-yl)Acetaminophen Adducts in Serum and liver Proteins of Acetaminophen-Treated Mice", *J Pharmacol Exp Ther*, 1989; 248:190–196, incorporated herein by reference, these assays were conducted by allowing a limiting amount of antibody to react with inhibitor, either standard or unknown, in the presence of excess solid phase antigen MDA/acetaldehyde modified proteins). After preliminary experiments, the following specific and optimal conditions were established to conduct the competitive ELISA assay: ELISA plate wells were coated with 100 μl of BSA that had been treated with 1 mM acetaldehyde and 1 mM MDA for 24 hours (approx. 2 μg/well). Biotinylated antibody (1/500 final dilution) was incubated with varying concentrations of test samples (standards or unknowns) overnight at 4° C., and then a 100 μl-aliquot of each sample was added to duplicate wells of the coated plates and incubated for 45 minutes at 37° C. After washing, 100 μl of alkaline phosphatase-conjugated streptavidin was added, and procedures as described above for the Direct ELISA were used to obtain optical density measurements. Results for each inhibitor concentration were expressed as % inhibition which was calculated using the following formula developed by Roberts et al (supra).

$$\% \text{ Inhibition} = \frac{(OD_{\max} - BKG) - (OD_{sample} - BKG)}{(OD_{\max} - BKG)} \times 100$$

where $OD_{max}$ is OD in the absence of inhibitor, BKG is OD from nonspecific absorption of assay reagents and $OD_{sample}$ is the OD for a given concentration of standard or unknown sample.

Preparation of Liver Cytosol From Ethanol-Fed and Control Rats:

Male Wistar Rats (150–160 g) were pair-fed the Lieber-DeCarli ethanol-containing and the control liquid diets, Lieber, et al., "The Feeding of Ethanol in Liquid Diets", 1986 Update, *Alcohol Clin Esp Res*, 1986; 10:550–553, incorporated herein by reference, for up to 5 weeks according to the methods in Casey, et al., "Chronic Ethanol Administration Impairs the Binding and Endocytosis of Asialoorosomucoid in Isolated Hepatocytes", *J Biol Chem*, 1987; 262:2704–2710, also incorporated herein. Isolated hepatocytes were prepared by collagenase perfusion as previously reported, and an hepatocyte cytosolic fraction was prepared by ultracentrifugation. Volentine, et al., Subcellular Location of Secretory Proteins Retained in the Liver During the Ethanol-Induced Inhibition of Hepatic Protein Secretion in the Rat", *Gastroenterology*, 1986; 90:158–165. Protein content of the cytosol fraction was determined by the method Lowry et al., "Protein Measurement with the Folin Phenol Reagent", *J Biol Chem*, 1951; 193:265–275. Aliquots of hepatocyte cytosolic proteins were analyzed for adducts by competitive ELISA on the same day of preparation.

Figure 1:
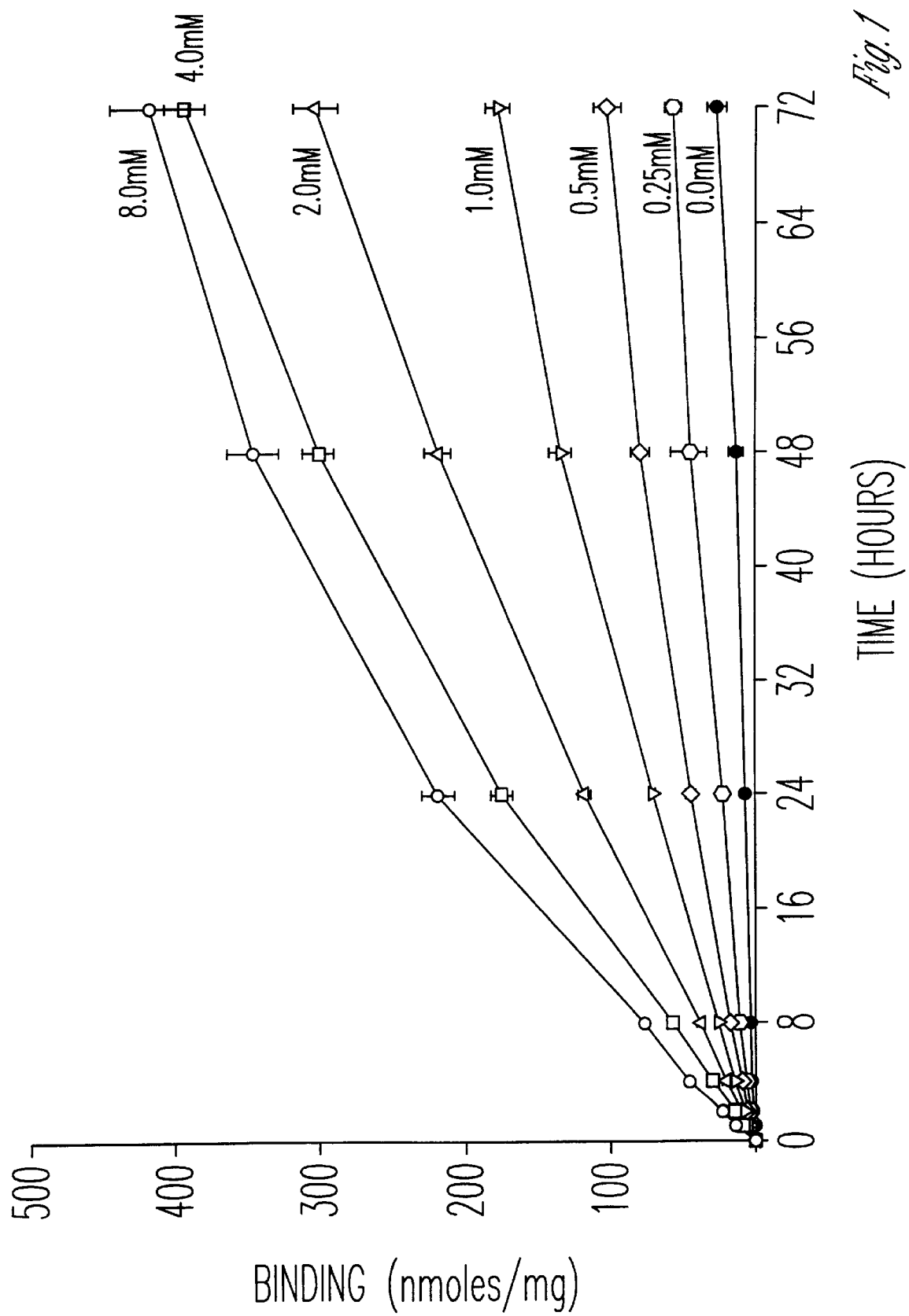
FIG. 1 is a graph demonstrating the synergistic action of MDA and acetaldehyde on the binding of bovine serum albumin (BSA). The graph depicts varying concentrations of MDA incubated in the presence of acetaldehyde (1 mM) over a 72-hour time course. Thus MDA markedly simulates the binding of acetaldehyde to BSA in a concentration dependent manner. Results are expressed as mean ±SE for five experiments.

The results illustrated in FIG. 1 demonstrate the dramatic effects of MDA on the stable binding of acetaldehyde to BSA. When acetaldehyde (1 mM) was incubated with bovine serum albumin (BSA) in the presence of varying concentrations of MDA over a 72-hour time course, MDA markedly stimulated the binding of acetaldehyde to BSA in a concentration-dependent manner. For example, after 24 hours of incubation, a 13-fold stimulation at a 4-fold molar excess of MDA were observed. It appeared that maximum stimulation of acetaldehyde binding occurred at about a 4 molar excess of MDA. The MDA-induced increase in acetaldehyde binding to BSA also was observed when lower concentrations of aldehydes were used. When acetaldehyde at 0.1 mM was incubated with MDA (0.1 to 0.4 mM), the MDA-stimulation of acetaldehyde binding to BSA was still apparent although the effect was somewhat attenuated at these lower concentrations (FIG. 2). In addition to BSA, other proteins that were tested also exhibited markedly enhanced binding to acetaldehyde in the presence of MDA. These included mouse plasma proteins, rabbit plasma proteins, hemoglobin, epidermal growth factor, polylysine and rat liver cytosol proteins.

Figure 3A:
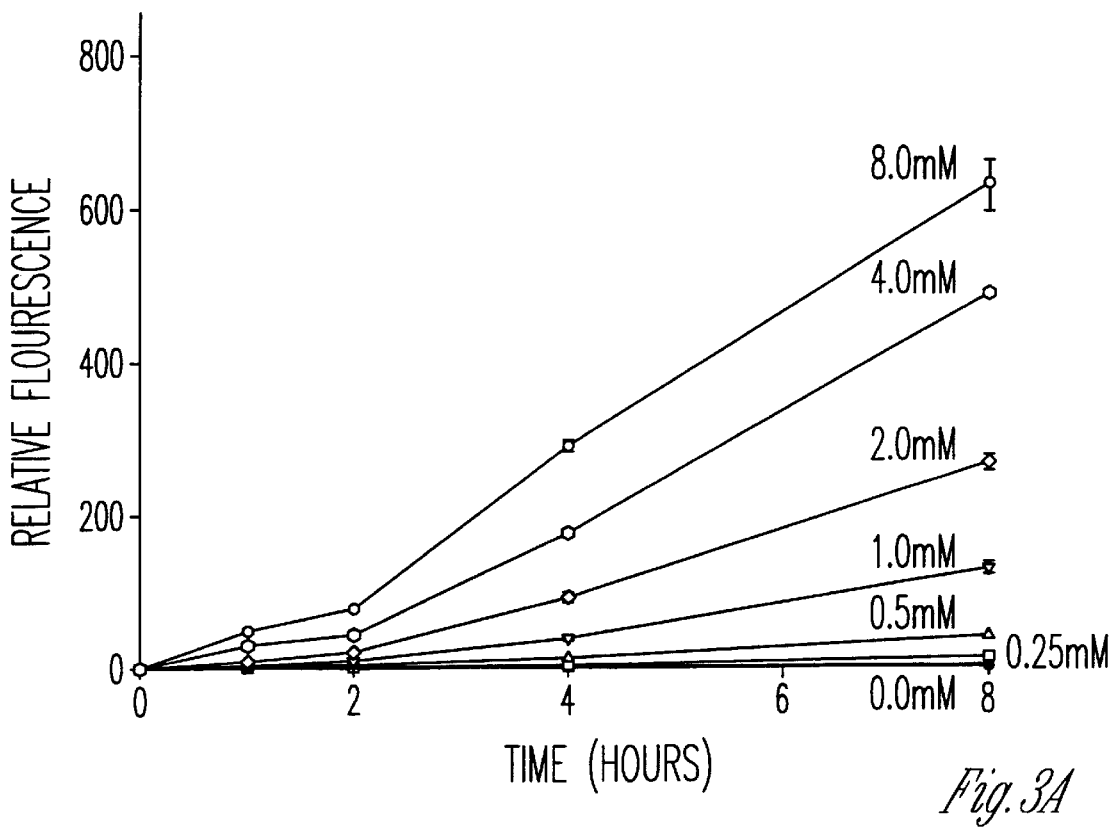
FIGS. 3(a) and (b) depict fluorescence intensities of reaction mixtures of BSA with acetaldehyde and MDA.
Figure 3B:
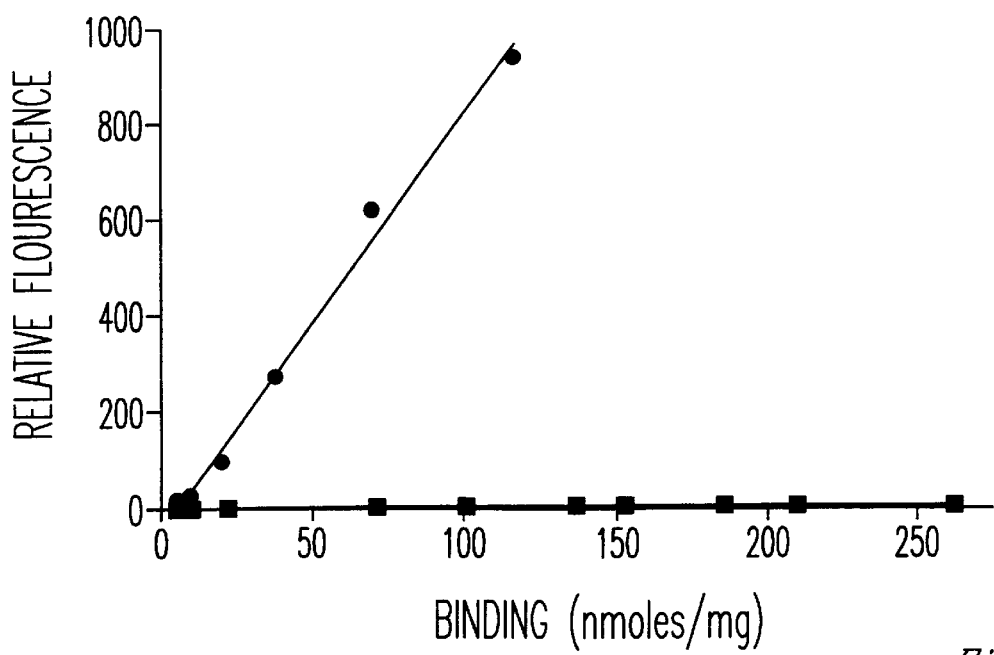
FIG. 3(b) is a graph depicting the relationship of acetaldehyde binding and fluorescence in the absence (square) and presence (circle) of MDA Reaction mixtures with MDA exhibited an absorbance maximum at 460 nm and in the absence of MDA the excitation and emission maxima was 357 nm and 440 nm, respectively.

The stimulation of acetaldehyde binding to BSA by MDA was accompanied by the formation of highly fluorescent products (FIG. 3A). Although previous studies have shown that reaction mixtures of BSA and high concentrations of acetaldehyde (<3 mM) alone also exhibited fluorescent properties, fluorescence observed in the presence of MDA was distinctly different. As shown in FIG. 3B, acetaldehyde binding in the presence of MDA resulted in the formation of extremely highly fluorescent products compared to the fluorescence associated with equivalent binding seen with acetaldehyde alone. In addition, the excitation and emission maxima were different for the two conditions (FIG. 3). When BSA was treated with MDA alone, fluorescence was also apparent, but was about 20–60 fold less over the MDA concentration ranges tested (0 to 8.0 mM) than that observed when acetaldehyde and MDA were both present. Thus, the stimulation of acetaldehyde binding to proteins by MDA is due to the formation of distinct products that differ from the products formed when proteins are treated with either acetaldehyde or MDA alone, MDA-acetaldehyde adducts (MAA).

Figure 4A:
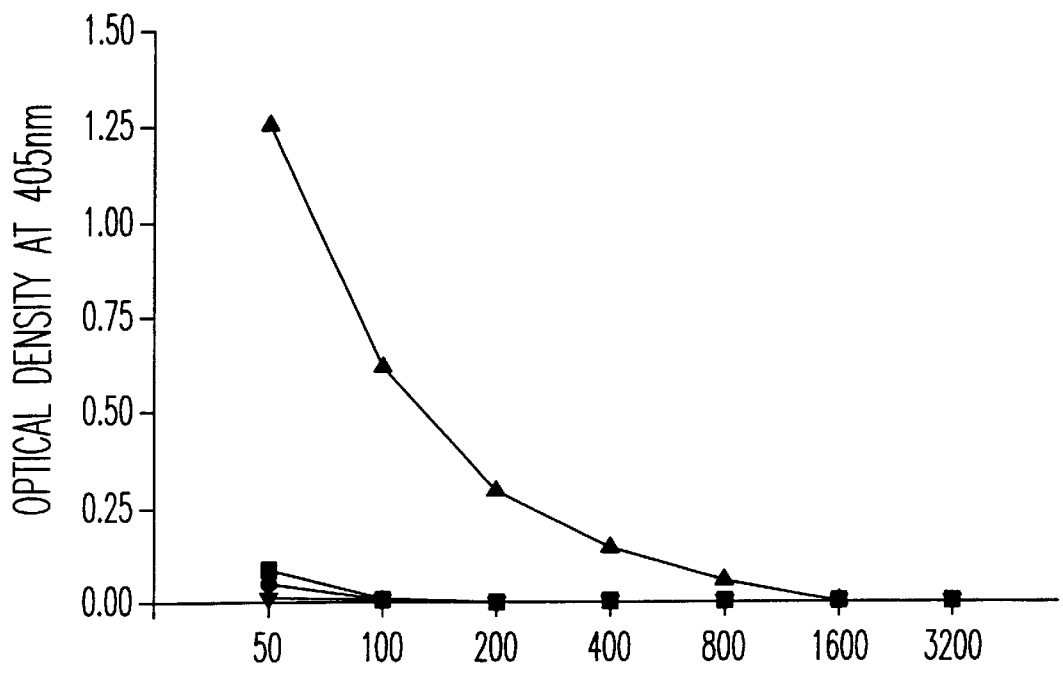
FIGS. 4(a) and 4(b) represent direct ELISA of the polyclonal antibodies from rabbit plasma protein-MAA conjugates against BSA-aldehyde conjugates to the MA-BSA adduct.
Figure 4B:
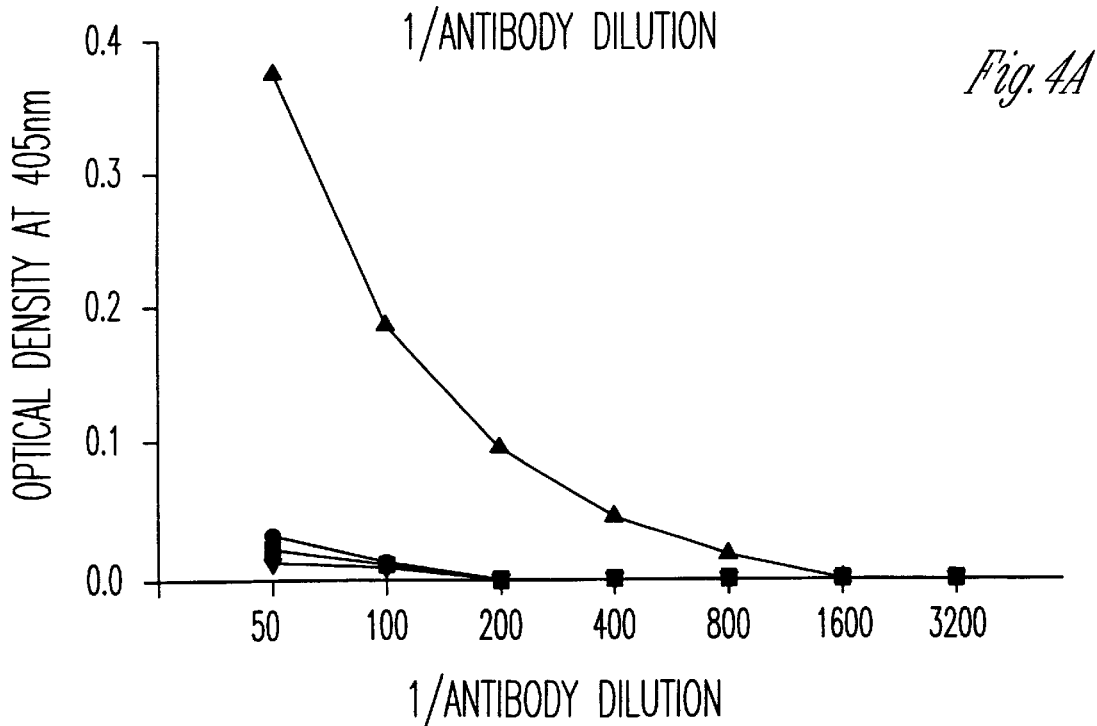

In subsequent experiments, an immunoassay was developed in order to detect the presence of MAA adducts in liver samples. A rabbit antibody was raised against the MAA adduct by immunizing the animals with rabbit plasma proteins-MAA adducts, and by purifying the antiserum in order to obtain an affinity purified IgG fraction that would recognize MAA adducts. The specificity of this antibody was tested by a direct ELISA against modified and unmodified BSA. The antibody recognized only BSA modified with MAA. The antibody had affinity for BSA modified with either 1 mM or 0.1 mM concentrations of both the aldehydes (FIG. 4). The antibody did not recognize native (unmodified) BSA or BSA modified with either acetaldehyde or MDA alone (FIG. 4). The specificity for MAA adducts was further tested with other proteins (e.g. rabbit plasma proteins, mouse plasma proteins, hemoglobin), and ELISA again demonstrated, as was the case with BSA, that this affinity purified antibody specifically recognized MAA epitopes on proteins.

Figure 5A:
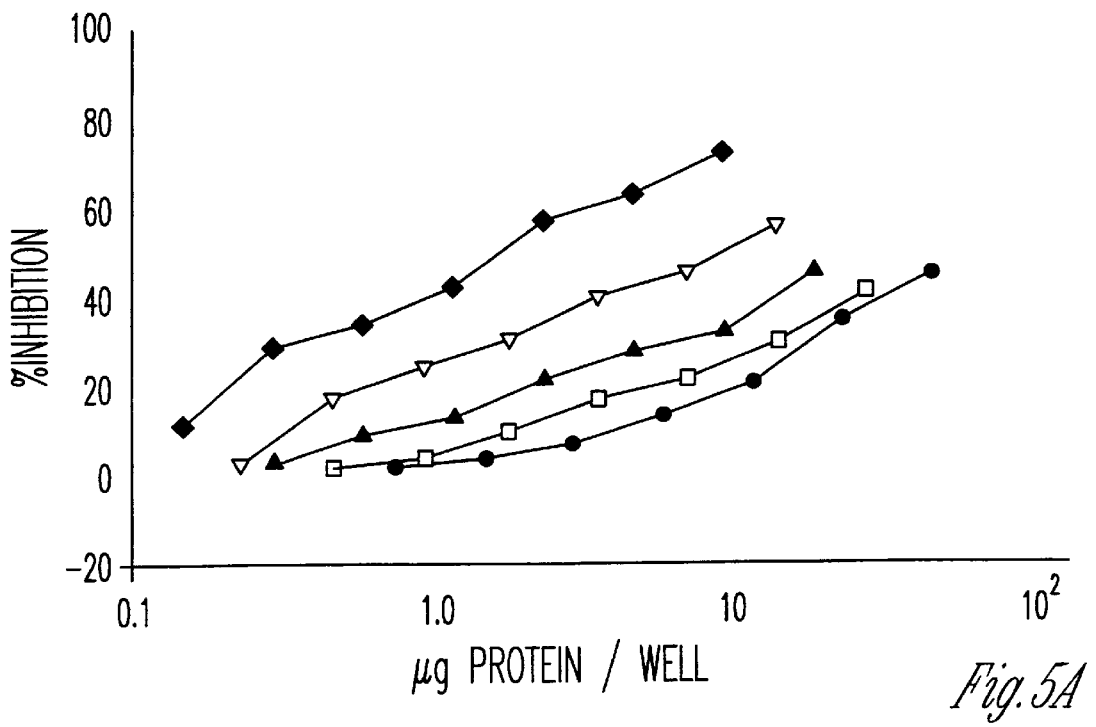
FIGS. 5(a) and 5(b) are graphs depicting the result of a competitive ELISA for competitive inhibition of BSA-MAA adducts, and the ability of variously MAA-modified BSA's to inhibit antibody binding. BSA was derivatized with varying concentrations of MDA and [$^{14}$C] acetaldehyde and stable binding of acetaldehyde was quantified. Degree of modification based on nmoles of acetaldehyde bound per mg of BSA were 28 (diamond); 15.4 (inverted triangle); 19.1 (triangle); 6.0 (square); and 3.5 (circle). 5(a) is a plot of percent inhibition of MAA adducts in terms of protein concentration. 5(b) depicts a plot of identical data as a function of bound acetaldehyde, indicating that the competitive ELISA adequately estimated the level of MAA modification of proteins and that the number of MAA epitopes is the most important determining factor in causing inhibition of antibody binding.
Figure 5B:
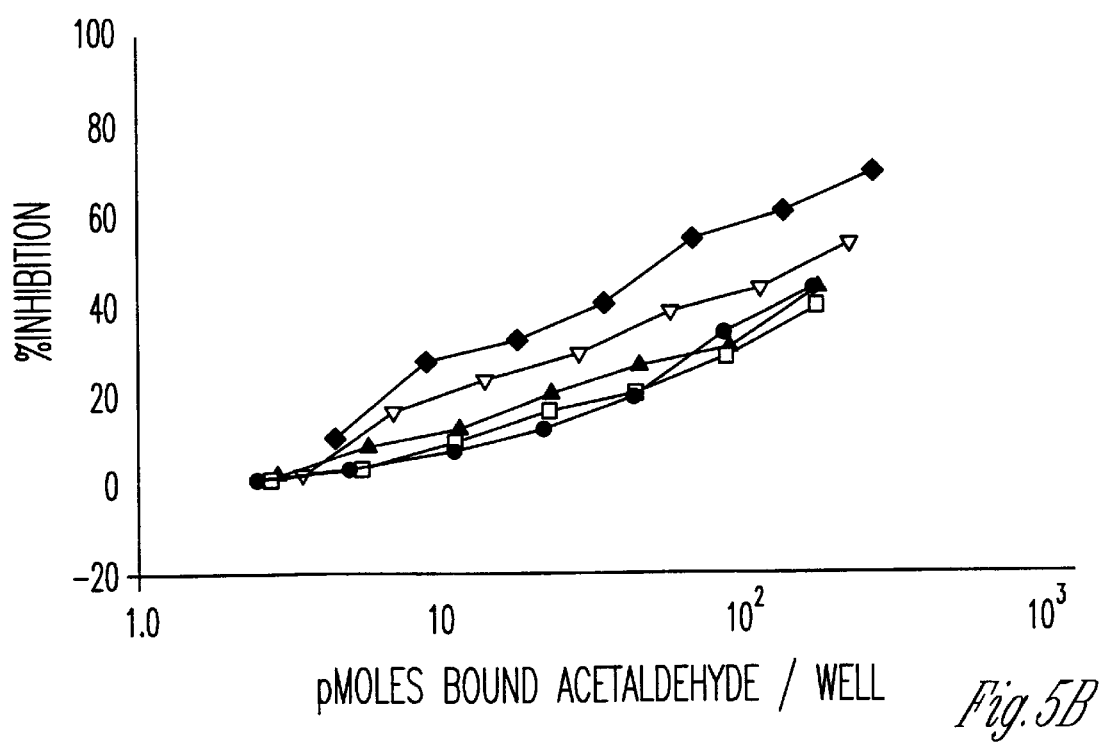
Figure 6A:
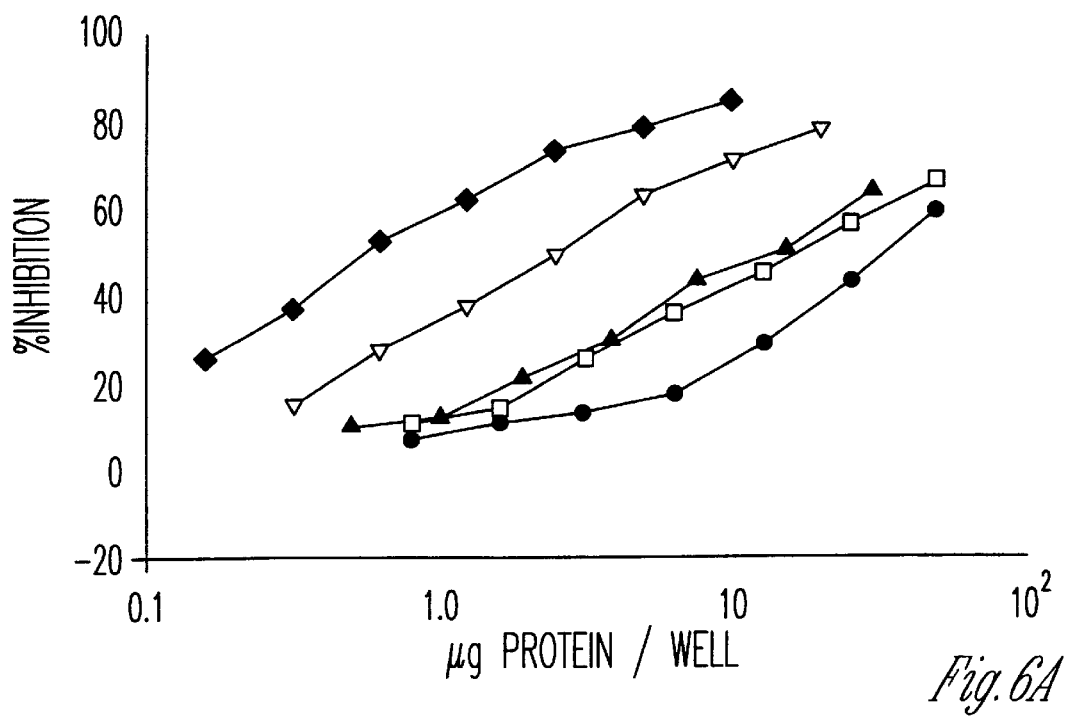
FIG. 6(a) is percent inhibition in terms of protein concentration bound acetaldehyde.
Figure 6B:
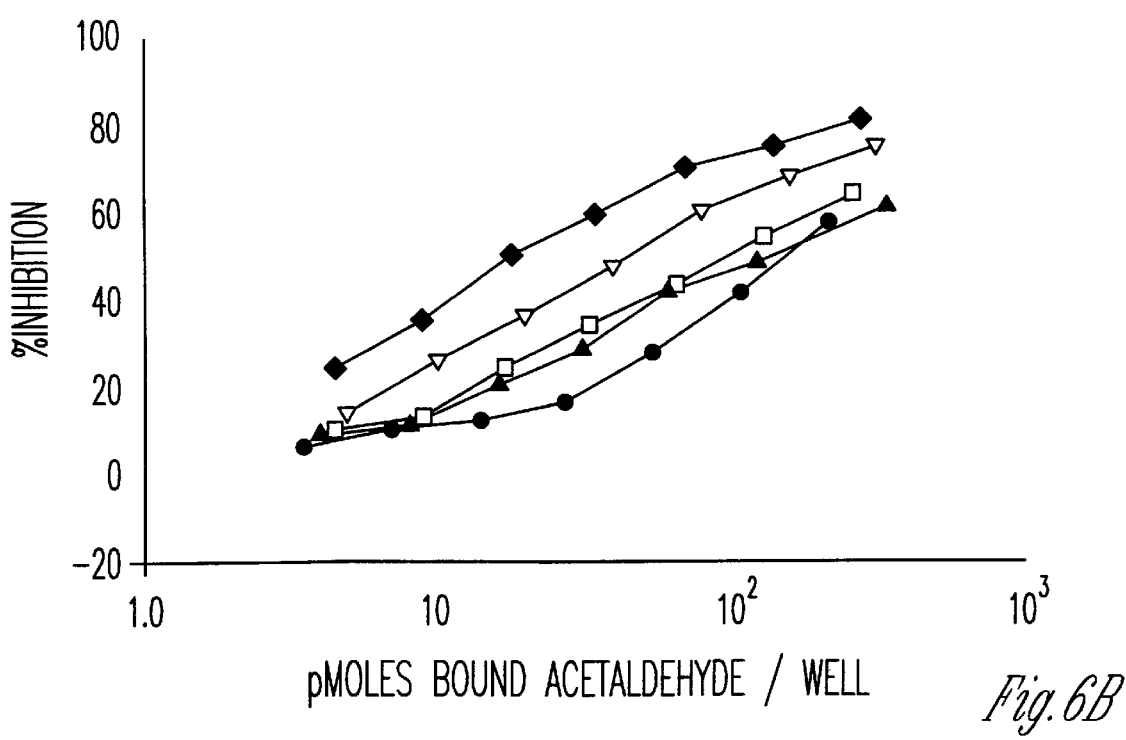
FIG. 6 represents competitive inhibition of cytosolic protein-MAA adducts in a competitive ELISA. Liver cytosolic proteins were derivatized with varying concentrations of MDA and [$^{14}$C] acetaldehyde and bound acetaldehyde was quantified. Degree of modification based on mmoles of acetaldehyde bound per mg liver cytosol proteins was 28.2 (diamond); 16.0 (inverted triangle); 8.1 (triangle); 6.2 (square); and 4.3 (circle).

This affinity purified antibody was then used in the development of a competitive ELISA in order to detect and quantify MAA adducts in liver samples. The applicability of this method was tested by preparing BSA at various levels of MAA derivatization. The substitution level of each modified BSA was determined by [$^{14}$C] radiolabeling, and the values on the level of MAA substitution were expressed as nmoles of acetaldehyde bound per mg of BSA. When these BSA-MAA adducts were tested in the competitive ELISA, the results showed an ordered family of inhibition curves where the most highly modified BSAs were the most efficient inhibitors, and the least substituted BSAs were the least efficient inhibitors when the % inhibitions were plotted as a function of BSA concentrations (FIG. 5A). On the other hand, when the same inhibition data were plotted as a function of MAA modification (i.e. acetaldehyde bound), the family of curves tended to become superimposed (FIG. 5B). These results indicated that the competitive ELISA could adequately estimate the level of MAA modification of proteins, and the number of MAA epitopes appeared to be the most important determining factor in causing inhibition of antibody binding. It should be pointed out, however, that under these conditions, inhibitions produced by MAA epitopes appeared to be more efficient in the more highly substituted BSAs (FIG. 5B). When the above experiments were repeated except that liver cytosol proteins were modified with MAA, similar inhibition curves were obtained as those observed for BSA-MAA (FIG. 6). In addition, native (untreated) liver cytosol proteins and liver cytosol proteins treated with MDA or acetaldehyde alone caused minimal to no inhibitions of antibody binding in the competitive ELISA. These results indicate the applicability of the competitive ELISA to detect and quantify MAA adducts in liver cytosol proteins, and similar procedures can be used to test other antibodies.

EXAMPLE 3

Figure 7A:
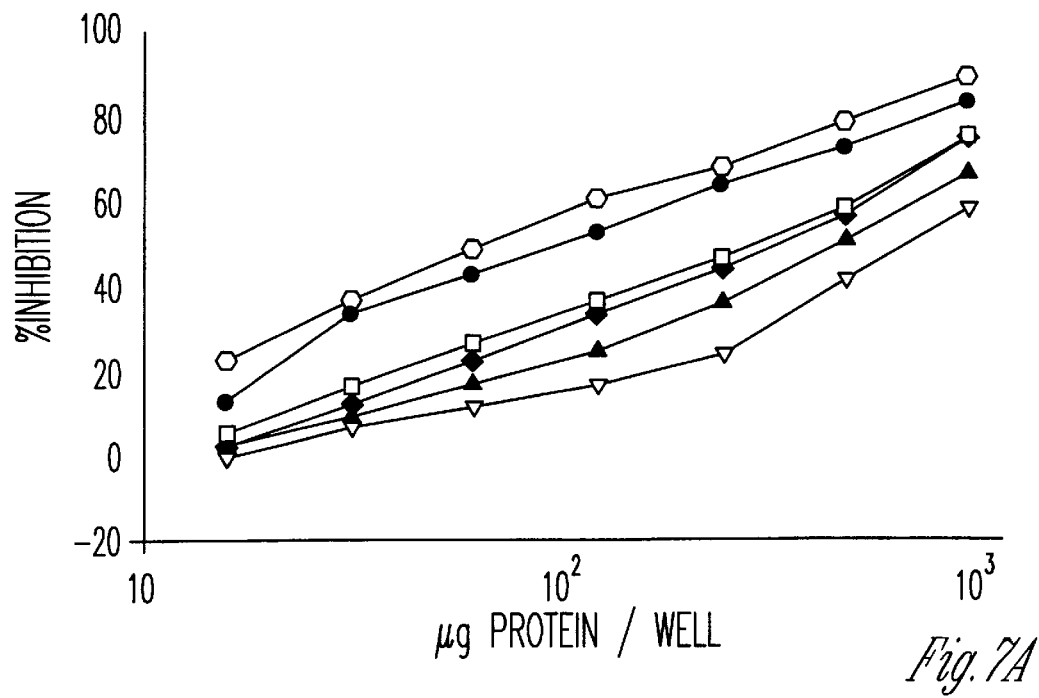
FIG. 7 is a competitive ELISA of minimally modified BSA-MAA adducts, using conditions of FIG. 5. Percent inhibition was determined based on nmoles of acetaldehyde bound per mg of BSA- 1.25 (hexagon); 1.00 (circle); 0.77
Figure 7B:
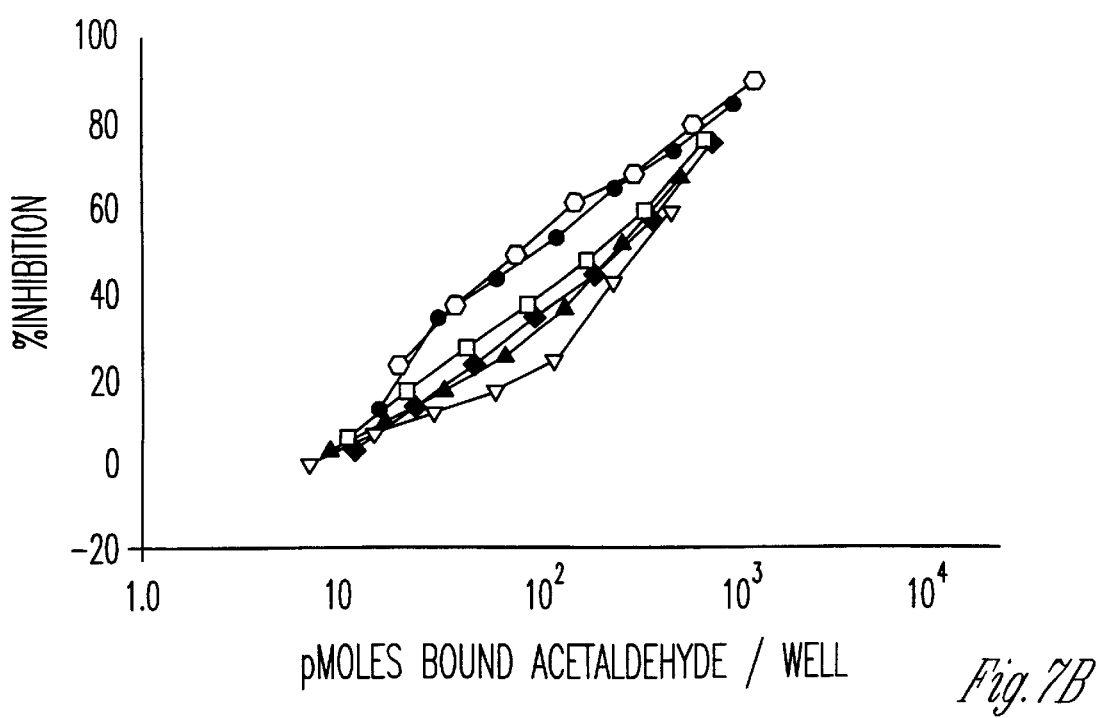

Further, experiments were conducted in order to verify the use of the competitive ELISA in the quantification of lowly modified MAA proteins. The data shown in FIGS. 5 and 6 indicated the number of MAA epitopes (i.e. acetaldehyde binding) that was necessary to be present in the assay mixture to produce sufficient inhibition of antibody binding in the competitive ELISA. Based upon the consideration of these data, the analysis of a large sample size (mg range) in the competitive ELISA for minimally modified proteins was dictated. In this case, when percent inhibition was plotted as a function of protein concentration, a family of inhibition curves were generated showing increased inhibition efficiencies with increasing degrees of MAA modification for both BSA-MAA (FIG. 7A) and liver cytosol proteins-MAA (FIG. 8A). However, when the inhibition data was plotted as a function of the number of MAA epitopes (i.e. acetaldehyde binding), the family of curves were superimposed for both the BSA-MAA (FIG. 7B) and liver cytosol proteins-MAA (FIG. 8B). These results confirmed the applicability of the competitive ELISA for the use of detecting and quantifying MAA epitopes on liver cytosol proteins.

The results of competitive ELISA in liver cytosol from two rats that were fed ethanol for 5 weeks and their corresponding pair-fed controls are shown in FIG. 9. MAA adducts were readily detected in the ethanol-fed rats as indicated by the inhibition curves for the liver cytosol obtained from these two ethanol-fed rats. Cytosol from control livers appeared to show only slight nonspecific inhibitions (FIG. 9A), and when these inhibition values were subtracted from the corresponding values from the ethanol-fed rats, inhibition curves were generated that represented an estimation of the quantity of MAA modifications of liver cytosol proteins from the ethanol-fed animals (FIG. 9B). Competitive ELISA assays were then conducted on liver cytosolic proteins from seven ethanol-fed rats and their corresponding pair-fed controls. When the inhibition curves generated by liver cytosol which was modified in, vitro with known substitution levels of MAA (FIG. 8B) were used as a standard curve, liver cytosol proteins from ethanol-fed rats were estimated to contain MAA adducts at the level of 75±14 pmoles of acetaldehyde bound per mg protein.

EXAMPLE 4

Unlike standard adjuvants, MAA is a specific immunoenhancing factor.

To demonstrate this aspect of MAA, applicants conducted several studies relating to immunogenicity in autologous and heterologous systems.

Antibody Responses in Autologous and Heterologous Systems

100 µg of normal plasma proteins modified with MAA were injected into autologous animals weekly over a 3 week period. The result was high antibody titers to only MAA (hapten), but not the normal protein. Thus, MAA did not create autoimmune disease in the animals, contrary to the effects of many hapten conjugates. This experiment was performed using rabbit, rat, and mouse plasma proteins.

Similarly, bovine serum albumin (BSA) modified with MAA was injected into mice at 100 µg/mouse without adjuvant. The result was high-titered antibody to both BSA and MAA. Also, BSA was injected into mice at 100 µg/mouse (no adjuvant) and the result was no antibody response to BSA or MAA. The results were generated by antibody titers cross-tested in ELISA and Western-Blot.

T-Helper Cell Responses in Autologous and Heterologous Systems

First, 100 µg of normal plasma proteins were injected into autologous animals weekly over a period of 3 weeks which resulted in no T cell response. Next, 100 µg of normal plasma proteins modified with MAA was injected into autologous animals weekly for three weeks which also resulted in no T cell response to MAA (the hapten).

However, there was a T-helper cell response to the normal plasma proteins (the carriers).

In heterologous systems, BSA was injected into animals in the same manner as set forth above with no adjuvant. The result was no T helper cell response to the BSA. When BSA modified with MAA was injected into mice, there was a T helper response to the BSA (the carrier), but not the MAA (hapten). This data was generated using T helper cell proliferations and cross-testing using many different carrier proteins. The experiments were repeated using human hemoglobin and transferrin, which generated similar data.

Immunization Studies

Prior to this time, all immunizations were performed by weekly injections over a 3 week interval. Animals were then bled and tested prior to each immunization. The purpose of these experiments were to determine what does and how many immunizations are necessary to get an antibody or T-helper cell response.

The first set of studies utilizing transferrin yielded the following results:

|  | Antibody Titer |
| --- | --- |
| MAA Adduction | |
| Doses of 100 μg of human transferrin-MAA | 62,500 |
| Doses of 50 μg of human transferrin-MAA | 62,500 |
| Doses of 10 μg of human transferrin-MAA | 2,500 |
| No MAA Adduction | |
| Doses of 100 μg of human transferrin | 2,500 |
| Doses of 10 μg of human transferrin | <100 |

Further Immunization Studies

The following immunization studies further demonstrate that MAA is not a general adjuvant or mitogen but specifically targets the conjugated protein to become immunogenic.

The applicants first took a 100 μg mixture of four proteins (25 μg each of human albumin, rabbit albumin, rat albumin and bovine albumin) and immunized mice with it once a week for three weeks. At the end of the fourth week mice were bled and serum tested for antibody to each of these proteins and two proteins that were not included in the immunization protocol. In two separate experiments: a) the bovine albumin was modified with MAA, b) none of the proteins were modified with MAA.

a) In the studies wherein the subjects were immunized with a mix of albumins wherein BSA was modified with MAA:

|  | Native | MAA |
| --- | --- | --- |
| Tested On | | |
| Human | <100 | 200 |
| Rabbit | 200 | 200 |
| Rat | <100 | 100 |
| Bovine | 8000 | 4000 |
| Negative Control | | |
| Chicken | <100 | 100 |
| Mouse | <100 | 200 | b) Where the subjects were immunized with a Immunized with mix of albumins wherein BSA was not modified:

|  | Native | MAA |
| --- | --- | --- |
| Tested On | | |
| Human | <100 | <100 |
| Rabbit | 100 | 100 |
| Rat | <100 | <100 |
| Bovine | 200 | 100 |
| Negative Control | | |
| Chicken | <100 | <100 |
| Mouse | <100 | <100 |

The data demonstrates that MAA targets the BSA to be taken up by antigen presenting cells and results in the production of a specific antibody response. If MAA was a polyclonal activator, then there should be a large amount of antibody to rat, rabbit and human proteins and this was not observed. There was some cross-reactivity to rabbit albumin and this may be related to a shared epitope and investigations are underway to determine whether this is true.

The data on the type of antibody response is very conclusive that primarily an IgG1 response to the MAA adduct is produced. These data are consistent with the observation that there is a strong T-helper cell response when utilizing MAA-adducted proteins. It is well known that IgM and IgG3 in the mouse are the predominant response when no T-cell help is observed with IgG1 and IgG2a production related to T-helper cells. In the above experiment a) the antibody to BSA is of the IgG1, IgG2a and IgG2b type. Similar results have been obtained with transferrin and hemoglobin.

The target for the proteins modified with MAA appear to be peritoneal macrophages. This is suggested because the data shows that the f-Alb scavenger receptor on liver endothelial cells avidly binds proteins modified with MAA. The only other place this receptor can be found is on peritoneal macrophages and all immunizations with mice have been performed giving intraperitoneal injections.

Modification of proteins with MAA appears to shorten the time course for the production of antibody. Animals were bled one week after immunization with 100 μg of BSA-MAA and the serum tested against unmodified and modified proteins. Within one week the mouse was producing antibody to the BSA that is of the IgG1 isotype with no subsequent increase in IgM antibody production.

The implications of the above experiments is that the generation of the B-cells for monoclonal antibody production could be accelerated significantly. Generally, most animals require 3 immunizations in Freund's or RIBI adjuvant over a 6 week period to get a sufficient IgG antibody response. These studies showed there is a decrease in this time frame, yield a higher specificity and decrease the polyclonal activation.

One application of this invention is a cheaper, more effective vaccine, eliminating the need for subsequent boosters.

In regard to labeled antibody techniques, MAA can be used in labeled antibody procedures to visualize antigen-antibody interactions by labeling antigens or antibodies. MAA adduction of antigen or antibody does not alter their activity, directly or indirectly.

FIGS. 3(a) and (b) depict fluorescence intensities of reaction mixtures of BSA with acetaldehyde and MDA.

FIG. 3(a) depicts the relative fluorescence over an 8 hour time course with acetaldehyde (1.0 mM) and BSA (1 mg/ml) at 37° C. at various concentrations of MDA (0 to 8.0 mM). Results are mean +SE for five experiments.

FIG. 3(b) is a graph depicting the relationship of acetaldehyde binding and fluorescence in the absence (square) and presence (circle) of MDA. Reaction mixtures with MDA exhibited an absorbance maximum at 460 nm and in the absence of MDA the excitation and emission maxima was 357 nm and 440 nm, respectively.

In regard to antibody by FACScan, MAA can be used as a universal label for enhancing the visualization of protein-protein interactions and for monitoring the purification of biological materials.

Due to its fluorescent properties, MAA and anti-MAA specific monoclonal antibodies can be used as a fluorescent antibody in FACScan, immunohistochemistry, etc. It may further be used in the evaluation of complex mixtures on high performance separation procedures. MAA presents the advantage of low cross-reactivity in contrast to prior antibodies.

EXAMPLE 5

Recently it was shown that the concomitant incubation of protein with MDA and AA synergistically increased the amount of adduction and resulted in the production of a new epitope (MAA). This epitope was shown to be immunogenic without the use of adjuvant and can be produced under conditions that begin to approach physiological levels (1 mM) of AA and MDA. The purpose of this study was to determine how modification of a soluble carrier protein with the MAA adduct alters the humoral immune response. Balb/c mice were immunized weekly by i.p. injection with 100 μg of either bovine serum albumin unmodified (BSA) or modified with MAA (BSA-MAA). Titration of antiserum was performed by ELISA on wells coated with either BSA, BSA-MAA, mouse serum albumin (MSA) and MSA-MAA. In further studies to examine the level of protein necessary to induce this immune response, 12 groups of mice (5/group) were immunized with one of the following six doses of BSA or BSA-MAA: 100 μg, 50 μg, 25 μg, 10 μg, 5 μg, and 1 μg. Results show that in mice immunized with 100 μg of BSA-MAA, serum antibody titers to both BSA and BSA-MAA reached maximal levels at 3 weeks (>1:3200). Further testing on MSA and MSA-MAA demonstrated a significant antibody titer to the MAA adduct, but no response to the autologous protein. In mice immunized with lower concentrations of BSA-MAA, antibody titers decreased in a dose dependent manner to both BSA and BSA-MAA (>1:3200 at 100 μg to 1:2000 at 25 μg). Surprisingly, antiserum from mice immunized with 25 μg of BSA-MAA recognized epitopes on the BSA polypeptide chain and not the MAA adduct itself. BSA without MAA adduction elicited a weak antibody response to only BSA and only at high doses (>50 μg). Therefore, these data indicate that the adduction of protein with MAA enhances their immunogenicity and further suggest that MAA adduction stimulates the targeting, processing, and/or presentation of the carrier protein to the humoral immune system.

EXAMPLE 6

Proteins (at 2 mg/ml) were incubated with 1 mM AA and/or 1 mM MDA for 3 days at 37° C. Rabbits were immunized subcutaneously with MAA-modified rabbit plasma proteins (RbPP) in Freunds' adjuvant. Mice were immunized intraperitoneally with MAA-modified mouse plasma proteins (MsPP) in Freunds' adjuvant. Polyclonal rabbit serum was affinity-purified to the MAA-adduct using lysine-Sepharose 4B beads modified with 1 mM MDA and 1 mM AA for 16 hours at 37° C. Antibody was purified using standard affinity chromatography methods. Spleen cells from mice immunized with MsPP-MAA were fused with myelomas using established methods to produce hybridomas secreting MAA-specific monoclonal antibodies that were purified using protein G. To determine specificity, the antisera and purified antibodies were titered against RbPP, MsPP and BSA modified with nothing, AA, MDA or MAA. Antisera from rabbits and mice had antibody titers of 1:12,800 and 1:6400, respectively to the MAA adduct and no titer to the syngeneic carrier protein. Both antisera showed minor reactivity to AA- and MDA-modified proteins (1:200 or less). Affinity purification of rabbit antibody and the production of mouse monoclonal antibodies resulted in high-titered antibody specific for only the MAA-adduct and capable of detecting MAA on a variety of different proteins. Recently, using a competitive inhibition ELISA, applicants have shown the presence of MAA-adducted proteins in the livers of rats chronically-fed alcohol. Therefore, the use of these antibodies may prove useful in determining the physiological relevance of MAA-associated proteins in the development and/or progression of ALD.

EXAMPLE 7

An immunological assay, using an affinity-purified polyclonal antibody specific for MAA adducts, was employed to detect the presence of these adducts in livers of ethanol-fed rats. Since MAA adducts are likely composed of more than one distinct product, applicants have proposed that 4-methyl-1,4-dihydropyridine-3,5-dicarbaldehyde (MDDC), derivatized to an ε-amino group of lysine, represents a structure for one of the major MAA-protein adducts. The purpose of this study was to characterize the antigen binding properties of the MAA specific antibody and determine whether MDDC epitopes are a major determinant of antibody recognition. A competitive ELISA, utilizing bovine serum albumin-MAA as the solid phase antigen, was used to test the binding specificity of the antibody. The most effective inhibitor of antibody binding in this assay, with a 50% inhibitory concentration of 4 pmoles/well, was 1-hexyl-MDDC, which simulates a MDDC group attached to a lysyl residue of a protein. Analogs of 1-methyl and 1-hydrogen MDDC had increased 50% inhibitory concentrations of 14 and 240 pmoles/well, respectively. Substitutions at the 4-position of MDDC had even greater effects. Replacement of the 4-methyl with a 4-hexyl or 4-cyclohexyl group resulted in 3800- and 20,000-fold increases in the 50% inhibitory concentrations, respectively. Endogenous liver compounds with structures related to 1-hexyl-MDDC, such as NADH and pyridoxal, produced negligible inhibitions of antibody binding. When 8 different MAA-adducted proteins were tested in the competitive ELISA and the resulting inhibitions expressed as a function of the number of lysyl-MDDC residues per protein, the 50% inhibitory concentrations of these various MAA-protein adducts ranged from 1 to 31 pmoles of lysyl-MDDC equivalents/well. Digestions of these proteins with pronase markedly narrowed the range of the observed 50% inhibitory concentrations (6 to 15 pmoles/well), indicating that protein hydrolysis equalized the accessibility of the antibody to bind the epitope on these various proteins. These results indicate that the MAA-adduct specific antibody predominantly recognizes the 1-lysyl MDDC residue on proteins and can be effectively used to detect and quantify MAA adducted proteins.

EXAMPLE 8

|  | Antibody Titered On | | | |
| --- | --- | --- | --- | --- |
|  | BSA | BSA-MAA | MSA | MSA-MAA |
| Immunized With |  |  |  |  |
| BSA | 400 | 400 | 100 | 100 |
| BSA-MAA | >3200 | >3200 | 800 | >3200 |
| MsPP | 400 | 800 | 200 | 400 |
| MsPP-MAA | 800 | >3200 | 800 | >3200 |
| Immunized with Freunds |  |  |  |  |
| BSA | >3200 | >3200 | 200 | 800 |
| BSA-MAA | >3200 | >3200 | >3200 | >3200 |
| MsPP | >3200 | >3200 | 200 | 800 |
| MsPP-MAA | 3200 | >3200 | >3200 | >3200 |

The above results demonstrate that while Freund's adjuvant increased the antibody activity to the different proteins, it also causes high background responses to BSA and MSA. MAA adduction only increases the response to those proteins modified, resulting in low backgrounds to other proteins with increased antibody titer to the carrier protein (specificity).

Therefore, immunization with soluble BSA or MSA results in low antibody responses while immunization with soluble BSA MAA causes a strong antibody response to BSA and MSA-MAA, with a small increase to MSA. Moreover, immunization with soluble MsPP-MAA develops a strong antibody response to MAA adducted proteins only.

The following study compared the titers of rabbit anti-transferrin antibody either unlabeled or labeled with MAA, by Western Blot analysis. Labeled or unlabeled antibodies were diluted as follows: 1:500, 1K, 2K, 4K, 6K, 8K and 16K. Each dilution was incubated on a strip, cut from a blot, generated from a preparative SDS-PAGE gel of purified transferrin. The transferrin antigen band contained approximately 2 $\mu$g of protein. Anti-transferrin activity was detected by an indirect method using alkaline phosphatase conjugated goat anti-rabbit IgG.

The results showed that the rabbit anti-transferrin antibody was sufficiently labeled with MAA as evidenced by fluorescent antibody staining on the blot strips. Also, there was no different in antibody titers between MAA-labeled and unlabeled antibody as detected by goat anti-transferrin antibody. Therefore, it was concluded that labeling antibody with MAA adducts does not interfere with its ability to combine with antigens.

Further support for the conclusion that MAA-protein adducts represent unique and distinct chemical structures can be obtained by consideration of the studies of Ohya. Ohya T. "Formation of a new 1,1,1 adduct in the reaction of malondialdehyde, n-hydroxylamine and alkanal under neutral conditions." Biol Pharm Bull 1993; 16:137–141. In his studies, investigating the reaction of MDA and alkanals with primary amines under neutral conditions, he observed the formation of two major products. These products were identified as a 1:1:1 adduct and a 2:1:1 adduct of MDA, alkanal and primary amine, respectively. If these findings are extrapolated to include the reaction of MDA and acetaldehyde with the $\epsilon$-amino group of lysine (or perhaps an $\alpha$-amino terminus as well) in proteins. The cyclic 2:1 adduct (FIG. 10B) has been shown to be highly fluorescent and, therefore, the formation of this adduct contributes to the fluorescence of MAA adducts observed in applicants' studies. In contrast to the complexity and heterogeneity associated with structural assignments for acetaldehyde-protein adduct and MDA-protein adducts, definitive chemical structures can be proposed for MAA adducts.

Another feature of MAA adduct formation with proteins is the production of immunodominant antigenic determinants. A high titer polyclonal antibody was raised in rabbits by immunization with rabbit plasma proteins that had been treated with only 1 mM concentrations of acetaldehyde and MDA. After affinity purification on MAA-lysine beads, the antibody showed a high specificity for MAA epitopes on proteins and did not react with acetaldehyde-treated, MDA-treated, or carrier proteins. The antibody recognized MAA epitopes on a variety of protein carriers which were modified with either high or low concentrations of aldehydes. This specific antibody was then used to develop an immunochemical assay for the detection and quantification of MAA adducts in biological samples.

A sensitive ELISA was developed to determine the extent of MAA modification of liver proteins during the chronic administration of ethanol to rats. The assay had a high specificity for MAA derivatives of proteins, and the extent of MAA modification was the most important factor in determining the efficiency of inhibition of antibody binding in this system. These factors indicate the applicability of this assay for not only the detection of MAA adducts but their quantification as well. When liver cytosol proteins, which were previously modified in vitro by low levels of MAA conjugation, were tested the assay proved to be effective in quantifying the extent of MAA modification in the pmolar range (FIG. 8). The quantification of MAA was based on pmoles of [$^{14}$C]acetaldehyde bound because it appears, based on the proposed structures of MAA adducts (FIG. 10), that there is one mole of acetaldehyde per mole of MAA derivative.

MAA-modified proteins in liver cytosol from ethanol-fed rats ere readily detected by the competitive ELISA; whereas, little or no immunoreactability to MAA adducts was observed in cytosol proteins from the pair-fed controls (FIG. 9). Quantification of the inhibition curves of the competitive ELISA indicated an estimate of MAA modification to be about 75 pmoles of MAA per mg of liver cytosol proteins of the ethanol-fed animals. Thus, significant formation of MAA adducts occurs on liver cytosol proteins during chronic ethanol administration to rats.

Numerous studies in the literature have applied immunochemical techniques to indicate the presence of a variety of protein adducts in the livers of ethanol-treated animals. These would include acetaldehyde adducts, MDA adducts, and more recently hydroxyethyl radical-derived adducts. However, structural information and epitope characterization of these adducts are lacking, and quantitative data have not been reported. In contrast, the applicants have provided quantitative estimates for MAA adduct formation and proposed structures of the MAA adducts. Furthermore, the results indicate that MDA and acetaldehyde react together in a synergistic manner which demonstrates that MAA adduct formation would be favored over adducts formed with acetaldehyde of MDA alone and that MAA adducts may represent a major species of adducts formed in the liver during ethanol metabolism. Since both the covalent binding of acetaldehyde to proteins and increased lipid peroxidation have been proposed as possible mediators of ethanol-induced liver injury, MAA protein-adduct formation represents an event dependent on both mechanisms, suggesting a common or unifying process (i.e. MAA adduct formation) by which both mechanisms can contribute to alcohol hepatotoxicity.

The above description sets forth novel MAA adducts useful as immunoenhancing factors. The description further provides methods of use for the novel adduct as a general fluorescent label for immunological techniques and methods for use of the adduct as a universal label for visualization of protein interactions and for monitoring purification of biological material. It is thus submitted that the present invention accomplishes at least all of its stated objectives.

What is claimed is:

1. A specific immune-enhancing factor comprising:
    a malondialdehyde-acetaldehyde adduct having the following formula:

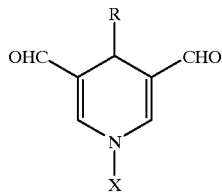

wherein X is an antigen containing an amino group; N is the nitrogen atom from said amino group; and R is selected from the group consisting of a lower $C_1$ to $C_6$ alkyl group, benzyl, and hydrogen.

2. The factor according to claim 1 wherein R is methyl.

3. The factor according to claim 1 wherein said antigen is selected from the group consisting of a carbohydrate, a DNA molecule, a protein, a peptide, and a lipid.

4. The factor of claim 1 wherein said antigen is of an animal origin.

5. The factor of claim 1 wherein said antigen is of an environmental origin.

6. The factor according to claim 1 which has an excitation frequency of about 398 nanometers and an absorbance of about 460 nanometers.

7. The factor of claim 1 wherein said antigen is of human origin.

8. The factor according to claim 1 wherein the antigen is selected from the group consisting of bovine serum albumin, human interferon, hemoglobin and human serum albumin.

9. A method for stimulating the immunogenicity of an antigen-comprising:
    contacting said antigen with malondialdehyde and acetaldehyde so that a malondialdehyde acetaldehyde adduct is formed, and introducing said malondialdehyde acetaldehyde adduct to the immune system of an animal.

10. The method of claim 9 wherein said antigen is introduced for vaccination purposes.

11. The method of claim 9 wherein said malondialdehyde acetaldehyde adduct stimulates the animal's immune system to produce antibodies to the antigen.

12. A method of claim 11 further including a method of detecting antigen/antibody complexes formed by the animal in response to the introduction of the adduct to the immune system of the animal.

13. The method of claim 12 wherein said detecting is by fluorescence detection.

14. The method of claim 9 wherein said malondialdehyde acetaldehyde adduct has the following formula:

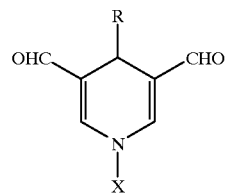

the formula wherein X is an antigen containing an amino group, N is the nitrogen atom in said amino group, and R is selected from the group consisting of a $C_1$ to $C_6$ alkyl group, benzyl, and hydrogen.

15. A malondialdehyde acetaldehyde adduct formed by the process of:
    contacting an antigen with malondialdehyde and acetaldehyde so that an adduct is formed.

16. The adduct of claim 15 wherein said adduct has the following formula:

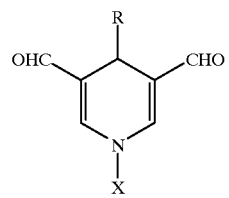

Wherein R is a $C_1$ to $C_6$ alkyl group, H, or Benzyl and X is a peptide or protein present in a biological sample, and further providing that N is a nitrogen atom from an amino group in the peptide or protein.

* * * * *